US012703763B2

(12) United States Patent
Chen et al.

(10) Patent No.: US 12,703,763 B2
(45) Date of Patent: Aug. 11, 2026

(54) ANTIBODIES BINDING C5 AND USES THEREOF

(71) Applicant: BIOSION INC., Nanjing (CN)

(72) Inventors: Mingjiu Chen, Nanjing (CN); Shukai Xia, Nanjing (CN)

(73) Assignee: BIOSION INC., Nanjing (CN)

( * ) Notice: Subject to any disclaimer, the term of this patent is extended or adjusted under 35 U.S.C. 154(b) by 805 days.

(21) Appl. No.: 18/004,912

(22) PCT Filed: Jul. 15, 2021

(86) PCT No.: PCT/CN2021/106391

§ 371 (c)(1),
(2) Date: Jan. 10, 2023

(87) PCT Pub. No.: WO2022/012606

PCT Pub. Date: Jan. 20, 2022

(65) Prior Publication Data

US 2023/0357438 A1 Nov. 9, 2023

Related U.S. Application Data

(60) Provisional application No. 63/051,966, filed on Jul. 15, 2020.

(51) Int. Cl.
*C07K 16/44* (2006.01)
*A61P 29/00* (2006.01)
*C12N 15/63* (2006.01)

(52) U.S. Cl.
CPC .............. *C07K 16/44* (2013.01); *A61P 29/00* (2018.01); *C12N 15/63* (2013.01); *C07K 2317/565* (2013.01)

(58) Field of Classification Search
None
See application file for complete search history.

(56) References Cited

U.S. PATENT DOCUMENTS 8,206,716 B2 * 6/2012 Fung .................. A61K 39/3955 435/7.1
2020/0385481 A1 12/2020 Song et al.

FOREIGN PATENT DOCUMENTS

| | | | |
|---|---|---|---|
| CN | 101443050 | A | 5/2009 |
| CN | 110603054 | A | 12/2019 |
| EP | 0411306 | A1 | 2/1991 |
| JP | 2017226655 | A | 12/2017 |
| WO | 9529697 | A1 | 11/1995 |
| WO | 2010015608 | A1 | 2/2010 |

OTHER PUBLICATIONS

C. Chen, et al., Role of C5a in inflammatory reaction and development of anti-C5a antibody drugs, Chinese Journal of Biologicals (May 31, 2015) vol. 28, No. 5, p. 547-552.
X. W. Wang, et al., Immunoglobulin VII Gene Expression in Human Aging, Clinical Immunology (Nov. 30, 1999) vol. 93, No. 2, p. 132-142.
International Search Report and Written Opinion issued Oct. 12, 2021 in Int'l Application No. PCT/CN2021/106391.
CNIPA, First Office Action issued Dec. 15, 2025 to counterpart Chinese application.
EPO, Supplementary Partial European Search Report and Written Opinion issued Nov. 8, 2023 to counterpart European application.
KIPO, First Office Action issued Nov. 29, 2025 to counterpart Korean application.
JPO, Notice of Reasons for Refusal issued Dec. 12, 2023 to counterpart Japanese application.
Adrianna Latuszek et al, Inhibition of complement pathway activation with Pozelimab, a fully human antibody to complement component C5, PLOS ONE, vol. 15, No. 5, May 8, 2020, p. e0231892.

* cited by examiner

*Primary Examiner* — Maher M Haddad
(74) *Attorney, Agent, or Firm* — Duane Morris LLP; Thomas J. Kowalski

(57) ABSTRACT

An isolated monoclonal antibody that specifically binds human C5, or the antigen-binding portion thereof. A nucleic acid molecule encoding the antibody or the antigen-binding portion thereof, an expression vector, a host cell and a method for expressing the antibody or the antigen-binding portion thereof are also provided. Further provided are a bispecific molecule, an immunoconjugate, a chimeric antigen receptor, an oncolytic virus and a pharmaceutical composition comprising the antibody or the antigen-binding portion thereof, as well as a treatment method using an anti-C5 antibody or the antigen-binding portion thereof.

15 Claims, 7 Drawing Sheets

Specification includes a Sequence Listing.

| | A5H1D11A7 | A5G2A1A1 | A3B4H8H7 | Eculizumab |
|---|---|---|---|---|
| EC50 | 0.05149 | 0.107 | 0.09766 | 0.8511 |

| | A2E12G12H7 | A5F3D5A1 | Eculizumab |
|---|---|---|---|
| EC50 | 0.04178 | 0.1083 | 0.7781 |

| | A4G10B7A7 | A3C8E4H1 | A6A1H9B7 | A5G9C2C7 | Eculizumab |
|---|---|---|---|---|---|
| EC50 | 0.09834 | 0.07374 | 0.1101 | 0.02771 | 0.8175 |

| | A5H1D11A7 | A5G2A1A1 | A3B4H8H7 | Eculizumab |
|---|---|---|---|---|
| EC50 | 0.1434 | 0.1404 | 0.1699 | 31.42 |

| | A2E12G12H7 | A5F3D5A1 | Eculizumab |
|---|---|---|---|
| EC50 | 0.1271 | 0.1517 | 151 |

| | A4G10B7A7 | A3C8E4H1 | A6A1H9B7 | A5G9C2C7 | Eculizumab |
|---|---|---|---|---|---|
| EC50 | 0.1613 | 0.1748 | 0.1671 | 0.1281 | 20.48 |

| | A5H1D11A7 | A5G2A1A1 | A3B4H8H7 | Eculizumab |
|---|---|---|---|---|
| EC50 | 0.1071 | 0.1058 | 0.161 | 1052 |

| | A2E12G12H7 | A5F3D5A1 | A4G10B7A7 | A3C8E4H1 | Eculizumab |
|---|---|---|---|---|---|
| EC50 | 0.06836 | 0.07158 | 0.08588 | 0.1388 | ~ 1.788e+014 |

| | A6A1H9B7 | A5G9C2C7 | Eculizumab |
|---|---|---|---|
| EC50 | 0.1431 | 0.0853 | ~ 9074 |

| | A5H1D11A7 | A5G2A1A1 | A3B4H8H7 | Eculizumab |
|---|---|---|---|---|
| IC50 | 0.1407 | 0.2141 | 0.3781 | 3.228 |

| | A2E12G12H7 | A5F3D5A1 | Eculizumab |
|---|---|---|---|
| IC50 | ~0.001528 | 0.3185 | 2.644 |

| | A4G10B7A7 | A3C8E4H1 | A6A1H9B7 | A5G9C2C7 | Eculizumab |
|---|---|---|---|---|---|
| IC50 | 0.1913 | 0.1445 | 0.09428 | ~0.2564 | 2.333 |

| | A5H1D11A7 | Pozelimab |
|---|---|---|
| IC50 | 0.1055 | 0.3294 |

| | Eculizumab | A5H1D11A7 | A2E12G12H7 | A5F3D5A1 |
|---|---|---|---|---|
| IC50 | 1.936 | 1.722 | 1.76 | 2.039 |

| | Eculizumab | A4G10B7A7 | A3C8E4H1 | A6A1H9B7 |
|---|---|---|---|---|
| IC50 | 2.039 | 1.83 | 1.863 | 1.86 |

| | Eculizumab | A5G2A1A1 | A3B4H8H7 | A5G9C2C7 |
|---|---|---|---|---|
| IC50 | 2.041 | 1.398 | 1.617 | 2.136 |

| | IC50 |
|---|---|
| Eculizumab | 127 |
| A5H1D11A7 | 108.9 |
| A3C8E4H1 | 110.6 |

SEQUENCE LISTING

```
<160> NUMBER OF SEQ ID NOS: 59

<210> SEQ ID NO 1
<211> LENGTH: 7
<212> TYPE: PRT
<213> ORGANISM: Artificial Sequence
<220> FEATURE:
<223> OTHER INFORMATION: VH CDR1 for A5H1D11A7

<400> SEQUENCE: 1

Ser Gly Ser Tyr Tyr Trp Ser
1               5


<210> SEQ ID NO 2
<211> LENGTH: 7
<212> TYPE: PRT
<213> ORGANISM: Artificial Sequence
<220> FEATURE:
```

<223> OTHER INFORMATION: VH CDR1 for A5G2A1A1 and A3C8E4H1

<400> SEQUENCE: 2

Ser Gly Ser Phe Tyr Trp Ser
1               5

<210> SEQ ID NO 3
<211> LENGTH: 5
<212> TYPE: PRT
<213> ORGANISM: Artificial Sequence
<220> FEATURE:
<223> OTHER INFORMATION: VH CDR1 for A2E12G12H7

<400> SEQUENCE: 3

Gly Tyr Tyr Ile His
1               5

<210> SEQ ID NO 4
<211> LENGTH: 5
<212> TYPE: PRT
<213> ORGANISM: Artificial Sequence
<220> FEATURE:
<223> OTHER INFORMATION: VH CDR1 for A3B4H8H7, A6A1H9B7, and A4G10B7A7

<400> SEQUENCE: 4

Ser Tyr Trp Ile Ser
1               5

<210> SEQ ID NO 5
<211> LENGTH: 8
<212> TYPE: PRT
<213> ORGANISM: Artificial Sequence
<220> FEATURE:
<223> OTHER INFORMATION: VH CDR1 for A5F3D5A1

<400> SEQUENCE: 5

Ser Tyr Trp Ile Ser Trp Val Arg
1               5

<210> SEQ ID NO 6
<211> LENGTH: 5
<212> TYPE: PRT
<213> ORGANISM: Artificial Sequence
<220> FEATURE:
<223> OTHER INFORMATION: VH CDR1 for A5G9C2C7

<400> SEQUENCE: 6

Gly Tyr Tyr Met His
1               5

<210> SEQ ID NO 7
<211> LENGTH: 16
<212> TYPE: PRT
<213> ORGANISM: Artificial Sequence
<220> FEATURE:
<223> OTHER INFORMATION: VH CDR2 for A5H1D11A7

<400> SEQUENCE: 7

His Ile Tyr Tyr Ser Gly Ser Thr Tyr Phe Asn Pro Ser Leu Lys Ser
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: VH CDR2 for A5G2A1A1 and A3C8E4H1

<400> SEQUENCE: 8

Tyr Ile Tyr Tyr Ser Gly Ser Thr Tyr Tyr Asn Pro Ser Leu Lys Ser
1 5 10 15

<210> SEQ ID NO 9
<211> LENGTH: 17
<212> TYPE: PRT
<213> ORGANISM: Artificial Sequence
<220> FEATURE:
<223> OTHER INFORMATION: VH CDR2 for A2E12G12H7

<400> SEQUENCE: 9

Trp Ile Asn Pro Asn Ser Gly Ser Thr Asn Ser Ala Gln Lys Phe Gln
1 5 10 15

Asp

<210> SEQ ID NO 10
<211> LENGTH: 17
<212> TYPE: PRT
<213> ORGANISM: Artificial Sequence
<220> FEATURE:
<223> OTHER INFORMATION: VH CDR2 for A3B4H8H7

<400> SEQUENCE: 10

Arg Ile Asp Pro Gly Asp Ser Tyr Thr Asn Asn Ser Pro Ser Phe Gln
1 5 10 15

Gly

<210> SEQ ID NO 11
<211> LENGTH: 17
<212> TYPE: PRT
<213> ORGANISM: Artificial Sequence
<220> FEATURE:
<223> OTHER INFORMATION: VH CDR2 for A6A1H9B7

<400> SEQUENCE: 11

Arg Ile Asp Pro Gly Asp Ser Tyr Ser Asn Phe Ser Pro Ser Phe Gln
1 5 10 15

Gly

<210> SEQ ID NO 12
<211> LENGTH: 17
<212> TYPE: PRT
<213> ORGANISM: Artificial Sequence
<220> FEATURE:
<223> OTHER INFORMATION: VH CDR2 for A4G10B7A7 and A5F3D5A1

<400> SEQUENCE: 12

Arg Ile Asp Pro Ser Asp Ser Tyr Thr Asn Asn Ser Pro Ser Phe Gln
1 5 10 15

Gly

<210> SEQ ID NO 13
<211> LENGTH: 17
<212> TYPE: PRT
<213> ORGANISM: Artificial Sequence
<220> FEATURE:
<223> OTHER INFORMATION: VH CDR2 for A5G9C2C7

<400> SEQUENCE: 13

Trp Ile Asn Pro Asn Ser Gly Gly Thr Asn Tyr Ala Gln Lys Phe Gln
1 5 10 15

Gly

<210> SEQ ID NO 14
<211> LENGTH: 10
<212> TYPE: PRT
<213> ORGANISM: Artificial Sequence
<220> FEATURE:
<223> OTHER INFORMATION: VH CDR3 for A5H1D11A7

<400> SEQUENCE: 14

Gly Tyr Gly Gly Tyr Gly Tyr Leu Asp Asn
1 5 10

<210> SEQ ID NO 15
<211> LENGTH: 10
<212> TYPE: PRT
<213> ORGANISM: Artificial Sequence
<220> FEATURE:
<223> OTHER INFORMATION: VH CDR3 for A5G2A1A1

<400> SEQUENCE: 15

Gly Tyr Ser Gly Tyr Gly Tyr Phe Asp Tyr
1 5 10

<210> SEQ ID NO 16
<211> LENGTH: 10
<212> TYPE: PRT
<213> ORGANISM: Artificial Sequence
<220> FEATURE:
<223> OTHER INFORMATION: VH CDR3 for A3C8E4H1

<400> SEQUENCE: 16

Gly Tyr Gly Gly Tyr Gly Tyr Leu Asp Tyr
1 5 10

<210> SEQ ID NO 17
<211> LENGTH: 15
<212> TYPE: PRT
<213> ORGANISM: Artificial Sequence
<220> FEATURE:
<223> OTHER INFORMATION: VH CDR3 for A2E12G12H7

<400> SEQUENCE: 17

Arg Ala Asp Tyr Tyr Gly Ser Gly Asn Phe Tyr Tyr Phe Asp Tyr
1 5 10 15

<210> SEQ ID NO 18
<211> LENGTH: 15
<212> TYPE: PRT
<213> ORGANISM: Artificial Sequence
<220> FEATURE:
<223> OTHER INFORMATION: VH CDR3 for A3B4H8H7, A6A1H9B7, A4G10B7A7, and A5F3D5A1

<400> SEQUENCE: 18

His His Pro Ile Leu Ala Thr Ile Ser Pro Asp Ala Phe Asp Ile
1 5 10 15

<210> SEQ ID NO 19
<211> LENGTH: 12
<212> TYPE: PRT
<213> ORGANISM: Artificial Sequence
<220> FEATURE:
<223> OTHER INFORMATION: VH CDR3 for A5G9C2C7

<400> SEQUENCE: 19

Glu Gly Leu Val Gly Val Ile His Gly Trp Asp Val 1 5 10

<210> SEQ ID NO 20
<211> LENGTH: 11
<212> TYPE: PRT
<213> ORGANISM: Artificial Sequence
<220> FEATURE:
<223> OTHER INFORMATION: VL CDR1 for A5H1D11A7, A5G2A1A1 and A3C8E4H1

<400> SEQUENCE: 20

Arg Ala Ser Gln Gly Ile Arg Asp Asp Leu Gly
1 5 10

<210> SEQ ID NO 21
<211> LENGTH: 11
<212> TYPE: PRT
<213> ORGANISM: Artificial Sequence
<220> FEATURE:
<223> OTHER INFORMATION: VL CDR1 for A2E12G12H7

<400> SEQUENCE: 21

Arg Ala Ser Gln Ser Ile Ser Arg Trp Leu Ala
1 5 10

<210> SEQ ID NO 22
<211> LENGTH: 12
<212> TYPE: PRT
<213> ORGANISM: Artificial Sequence
<220> FEATURE:
<223> OTHER INFORMATION: VL CDR1 for A3B4H8H7 and A6A1H9B7

<400> SEQUENCE: 22

Arg Ala Ser Gln Ser Phe Ser Ser Arg Tyr Leu Ala
1 5 10

<210> SEQ ID NO 23
<211> LENGTH: 12
<212> TYPE: PRT
<213> ORGANISM: Artificial Sequence
<220> FEATURE:
<223> OTHER INFORMATION: VL CDR1 for A4G10B7A7 and A5F3D5A1

<400> SEQUENCE: 23

Arg Ala Ser Gln Ser Ile Ser Ser Arg Tyr Leu Ala
1 5 10

<210> SEQ ID NO 24
<211> LENGTH: 11
<212> TYPE: PRT
<213> ORGANISM: Artificial Sequence
<220> FEATURE:
<223> OTHER INFORMATION: VL CDR1 for A5G9C2C7

<400> SEQUENCE: 24

Arg Ala Ser Gln Asn Ile Tyr Asn Trp Leu Ala
1 5 10

<210> SEQ ID NO 25
<211> LENGTH: 7
<212> TYPE: PRT
<213> ORGANISM: Artificial Sequence
<220> FEATURE:
<223> OTHER INFORMATION: VL CDR2 for A5H1D11A7 and A3C8E4H1

<400> SEQUENCE: 25

Ala Ala Ser Thr Leu Gln Ser
1 5

<210> SEQ ID NO 26
<211> LENGTH: 7
<212> TYPE: PRT
<213> ORGANISM: Artificial Sequence
<220> FEATURE:
<223> OTHER INFORMATION: VL CDR2 for A5G2A1A1

<400> SEQUENCE: 26

Ala Ala Ser Ser Leu Gln Ser
1 5

<210> SEQ ID NO 27
<211> LENGTH: 7
<212> TYPE: PRT
<213> ORGANISM: Artificial Sequence
<220> FEATURE:
<223> OTHER INFORMATION: VL CDR2 for A2E12G12H7

<400> SEQUENCE: 27

Ala Ala Thr Ser Leu Gln Ser
1 5

<210> SEQ ID NO 28
<211> LENGTH: 7
<212> TYPE: PRT
<213> ORGANISM: Artificial Sequence
<220> FEATURE:
<223> OTHER INFORMATION: VL CDR2 for A3B4H8H7 and A6A1H9B7

<400> SEQUENCE: 28

Gly Ala Ile Ser Arg Ala Thr
1 5

<210> SEQ ID NO 29
<211> LENGTH: 7
<212> TYPE: PRT
<213> ORGANISM: Artificial Sequence
<220> FEATURE:
<223> OTHER INFORMATION: VL CDR2 for A4G10B7A7 and A5F3D5A1

<400> SEQUENCE: 29

Ala Thr Ile Arg Arg Ala Thr
1 5

<210> SEQ ID NO 30
<211> LENGTH: 7
<212> TYPE: PRT
<213> ORGANISM: Artificial Sequence
<220> FEATURE:
<223> OTHER INFORMATION: VL CDR2 for A5G9C2C7

<400> SEQUENCE: 30

Lys Ala Ser Ser Leu Glu Ser
1 5

<210> SEQ ID NO 31
<211> LENGTH: 9
<212> TYPE: PRT
<213> ORGANISM: Artificial Sequence
<220> FEATURE:
<223> OTHER INFORMATION: VL CDR3 for A5H1D11A7

<400> SEQUENCE: 31

Leu Gln Asp Ser Asn Tyr Pro Trp Thr
1 5

<210> SEQ ID NO 32
<211> LENGTH: 9
<212> TYPE: PRT
<213> ORGANISM: Artificial Sequence
<220> FEATURE:
<223> OTHER INFORMATION: VL CDR3 for A5G2A1A1

<400> SEQUENCE: 32

Leu Gln Asp Asn Asn Phe Pro Trp Thr
1               5

<210> SEQ ID NO 33
<211> LENGTH: 9
<212> TYPE: PRT
<213> ORGANISM: Artificial Sequence
<220> FEATURE:
<223> OTHER INFORMATION: VL CDR3 for A3C8E4H1

<400> SEQUENCE: 33

Leu Gln Asp His Asn Tyr Pro Trp Thr
1               5

<210> SEQ ID NO 34
<211> LENGTH: 9
<212> TYPE: PRT
<213> ORGANISM: Artificial Sequence
<220> FEATURE:
<223> OTHER INFORMATION: VL CDR3 for A2E12G12H7

<400> SEQUENCE: 34

Gln Gln Ala Asn Thr Phe Pro Leu Ile
1               5

<210> SEQ ID NO 35
<211> LENGTH: 9
<212> TYPE: PRT
<213> ORGANISM: Artificial Sequence
<220> FEATURE:
<223> OTHER INFORMATION: VL CDR3 for A3B4H8H7 and A6A1H9B7

<400> SEQUENCE: 35

Gln Tyr Tyr Gly Ile Ser Pro Tyr Thr
1               5

<210> SEQ ID NO 36
<211> LENGTH: 9
<212> TYPE: PRT
<213> ORGANISM: Artificial Sequence
<220> FEATURE:
<223> OTHER INFORMATION: VL CDR3 for A4G10B7A7 and A5F3D5A1

<400> SEQUENCE: 36

Gln Lys Tyr Ser Ile Ser Pro Tyr Thr
1               5

<210> SEQ ID NO 37
<211> LENGTH: 9
<212> TYPE: PRT
<213> ORGANISM: Artificial Sequence
<220> FEATURE:
<223> OTHER INFORMATION: VL CDR3 for A5G9C2C7

<400> SEQUENCE: 37

Gln Gln Tyr Asn Ser Asn Ser Arg Thr
1               5

```
<210> SEQ ID NO 38
<211> LENGTH: 120
<212> TYPE: PRT
<213> ORGANISM: Artificial Sequence
<220> FEATURE:
<223> OTHER INFORMATION: VH for A5H1D11A7

<400> SEQUENCE: 38

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Leu Ser Ser Gly
            20                  25                  30

Ser Tyr Tyr Trp Ser Trp Ile Arg Gln His Pro Gly Lys Gly Leu Glu
        35                  40                  45

Trp Ile Gly His Ile Tyr Tyr Ser Gly Ser Thr Tyr Phe Asn Pro Ser
    50                  55                  60

Leu Lys Ser Arg Leu Thr Met Ser Val Asp Thr Ser Lys Asn Gln Phe
65                  70                  75                  80

Ser Leu Arg Leu Ser Ser Val Thr Ala Ala Asp Thr Ala Val Tyr Tyr
                85                  90                  95

Cys Ala Arg Gly Tyr Gly Gly Tyr Gly Tyr Leu Asp Asn Trp Gly Gln
            100                 105                 110

Gly Thr Leu Val Thr Val Ser Ser
        115                 120


<210> SEQ ID NO 39
<211> LENGTH: 120
<212> TYPE: PRT
<213> ORGANISM: Artificial Sequence
<220> FEATURE:
<223> OTHER INFORMATION: VH for A5G2A1A1 and A3C8E4H1
<220> FEATURE:
<221> NAME/KEY: misc_feature
<222> LOCATION: (29)..(29)
<223> OTHER INFORMATION: Xaa can be Ile or Leu
<220> FEATURE:
<221> NAME/KEY: misc_feature
<222> LOCATION: (71)..(71)
<223> OTHER INFORMATION: Xaa can be Ile or Met
<220> FEATURE:
<221> NAME/KEY: misc_feature
<222> LOCATION: (102)..(102)
<223> OTHER INFORMATION: Xaa can be Ser or Gly
<220> FEATURE:
<221> NAME/KEY: misc_feature
<222> LOCATION: (107)..(107)
<223> OTHER INFORMATION: Xaa can be Phe or Leu

<400> SEQUENCE: 39

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Xaa Ser Ser Gly
            20                  25                  30

Ser Phe Tyr Trp Ser Trp Ile Arg Gln Leu Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Leu Thr Xaa Ser Val Asp Pro Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Tyr Xaa Gly Tyr Gly Tyr Xaa Asp Tyr Trp Gly Gln
            100                 105                 110
```

```
Gly Thr Leu Val Thr Val Ser Ser
        115                 120


<210> SEQ ID NO 40
<211> LENGTH: 124
<212> TYPE: PRT
<213> ORGANISM: Artificial Sequence
<220> FEATURE:
<223> OTHER INFORMATION: VH for A2E12G12H7

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Ser Thr Asn Ser Ala Gln Lys Phe
    50                  55                  60

Gln Asp Trp Val Thr Leu Thr Arg Asp Thr Ser Ile Ser Thr Ala Tyr
65                  70                  75                  80

Met Glu Leu Ser Arg Leu Lys Ser Asp Asp Thr Ala Val Tyr Tyr Cys
                85                  90                  95

Ala Arg Arg Ala Asp Tyr Tyr Gly Ser Gly Asn Phe Tyr Tyr Phe Asp
            100                 105                 110

Tyr Trp Gly Gln Gly Thr Leu Val Thr Val Ser Ser
        115                 120


<210> SEQ ID NO 41
<211> LENGTH: 124
<212> TYPE: PRT
<213> ORGANISM: Artificial Sequence
<220> FEATURE:
<223> OTHER INFORMATION: VH for A3B4H8H7 and A6A1H9B7
<220> FEATURE:
<221> NAME/KEY: misc_feature
<222> LOCATION: (58)..(58)
<223> OTHER INFORMATION: Xaa can be Thr or Ser
<220> FEATURE:
<221> NAME/KEY: misc_feature
<222> LOCATION: (60)..(60)
<223> OTHER INFORMATION: Xaa can be Asn or Phe

<400> SEQUENCE: 41

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Arg Ile Asp Pro Gly Asp Ser Tyr Xaa Asn Xaa Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His His Pro Ile Leu Ala Thr Ile Ser Pro Asp Ala Phe Asp
            100                 105                 110

Ile Trp Gly Gln Gly Thr Met Val Thr Val Ser Ser
        115                 120
```

<210> SEQ ID NO 42
<211> LENGTH: 124
<212> TYPE: PRT
<213> ORGANISM: Artificial Sequence
<220> FEATURE:
<223> OTHER INFORMATION: VH for A4G10B7A7 and A5F3D5A1
<220> FEATURE:
<221> NAME/KEY: misc_feature
<222> LOCATION: (74)..(74)
<223> OTHER INFORMATION: Xaa can be Arg or Lys

<400> SEQUENCE: 42

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
            20                  25                  30

Trp Ile Ser Trp Val Arg Gln Met Pro Gly Lys Gly Leu Glu Trp Met
        35                  40                  45

Gly Arg Ile Asp Pro Ser Asp Ser Tyr Thr Asn Asn Ser Pro Ser Phe
    50                  55                  60

Gln Gly His Val Thr Ile Ser Val Asp Xaa Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His His Pro Ile Leu Ala Thr Ile Ser Pro Asp Ala Phe Asp
            100                 105                 110

Ile Trp Gly Gln Gly Thr Met Val Thr Val Ser Ser
        115                 120
```

<210> SEQ ID NO 43
<211> LENGTH: 121
<212> TYPE: PRT
<213> ORGANISM: Artificial Sequence
<220> FEATURE:
<223> OTHER INFORMATION: VH for A5G9C2C7

<400> SEQUENCE: 43

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Trp Val Thr Met Thr Arg Asp Thr Ser Ile Ser Thr Ala Tyr
65                  70                  75                  80

Met Glu Leu Arg Arg Leu Arg Ser Asp Asp Thr Ala Val Tyr Tyr Cys
                85                  90                  95

Ala Arg Glu Gly Leu Val Gly Val Ile His Gly Trp Asp Val Trp Gly
            100                 105                 110

Gln Gly Thr Thr Val Thr Val Ser Ser
        115                 120
```

<210> SEQ ID NO 44
<211> LENGTH: 107
<212> TYPE: PRT
<213> ORGANISM: Artificial Sequence
<220> FEATURE:

<223> OTHER INFORMATION: VL for A5H1D11A7 and A3C8E4H1
<220> FEATURE:
<221> NAME/KEY: misc_feature
<222> LOCATION: (18)..(18)
<223> OTHER INFORMATION: Xaa can be Ser or Thr
<220> FEATURE:
<221> NAME/KEY: misc_feature
<222> LOCATION: (92)..(92)
<223> OTHER INFORMATION: Xaa can be Ser or His
<220> FEATURE:
<221> NAME/KEY: misc_feature
<222> LOCATION: (106)..(106)
<223> OTHER INFORMATION: Xaa can be Phe or Ile

<400> SEQUENCE: 44

Ala Ile Gln Met Thr Gln Ser Pro Ser Ser Leu Ser Ala Ser Val Gly
1 5 10 15

Asp Xaa Val Thr Ile Thr Cys Arg Ala Ser Gln Gly Ile Arg Asp Asp
20 25 30

Leu Gly Trp Tyr Gln Gln Lys Pro Gly Lys Ala Pro Lys Leu Leu Ile
35 40 45

Phe Ala Ala Ser Thr Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Leu Gln Asp Xaa Asn Tyr Pro Trp
85 90 95

Thr Phe Gly Gln Gly Thr Lys Val Glu Xaa Lys
100 105

<210> SEQ ID NO 45
<211> LENGTH: 107
<212> TYPE: PRT
<213> ORGANISM: Artificial Sequence
<220> FEATURE:
<223> OTHER INFORMATION: VL for A2E12G12H7

<400> SEQUENCE: 45

Asp Ile Gln Met Thr Gln Ser Pro Ser Ser Val Ser Ala Ser Val Gly
1 5 10 15

Asp Arg Val Thr Ile Ser Cys Arg Ala Ser Gln Ser Ile Ser Arg Trp
20 25 30

Leu Ala Trp Tyr Gln Gln Lys Pro Gly Lys Ala Pro Lys Leu Leu Ile
35 40 45

Tyr Ala Ala Thr Ser Leu Gln Ser Gly Val Pro Ser Arg Phe Ser Gly
50 55 60

Ser Gly Phe Val Arg Asp Phe Thr Leu Thr Ile Ser Ser Leu Gln Pro
65 70 75 80

Glu Asp Phe Ala Thr Tyr Tyr Cys Gln Gln Ala Asn Thr Phe Pro Leu
85 90 95

Ile Phe Gly Gly Gly Thr Lys Val Glu Ile Lys
100 105

<210> SEQ ID NO 46
<211> LENGTH: 108
<212> TYPE: PRT
<213> ORGANISM: Artificial Sequence
<220> FEATURE:
<223> OTHER INFORMATION: VL for A3B4H8H7 and A6A1H9B7

<400> SEQUENCE: 46

Glu Ile Val Leu Thr Gln Ser Pro Gly Thr Leu Ala Leu Ser Pro Gly

```
1               5                   10                  15

Glu Arg Ala Thr Leu Ser Cys Arg Ala Ser Gln Ser Phe Ser Ser Arg
            20                  25                  30

Tyr Leu Ala Trp His Gln Gln Lys Pro Gly Gln Ala Pro Arg Leu Leu
        35                  40                  45

Ile Phe Gly Ala Ile Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr His Cys Gln Tyr Tyr Gly Ile Ser Pro
                85                  90                  95

Tyr Thr Phe Gly Gln Gly Thr Lys Leu Glu Ile Lys
            100                 105


<210> SEQ ID NO 47
<211> LENGTH: 108
<212> TYPE: PRT
<213> ORGANISM: Artificial Sequence
<220> FEATURE:
<223> OTHER INFORMATION: VL for A4G10B7A7 and A5F3D5A1

<400> SEQUENCE: 47

Glu Ile Val Leu Thr Gln Ser Pro Asp Thr Leu Ser Leu Ser Pro Gly
1               5                   10                  15

Glu Arg Ala Thr Leu Ser Cys Arg Ala Ser Gln Ser Ile Ser Ser Arg
            20                  25                  30

Tyr Leu Ala Trp Phe Gln Gln Lys Pro Gly Gln Ala Pro Arg Leu Leu
        35                  40                  45

Ile His Ala Thr Ile Arg Arg Ala Thr Gly Ile Pro Asp Arg Phe Ser
    50                  55                  60

Gly Ser Gly Ser Gly Thr Asp Phe Thr Leu Thr Ile Ser Gly Leu Glu
65                  70                  75                  80

Pro Glu Asp Phe Ala Val Tyr Tyr Cys Gln Lys Tyr Ser Ile Ser Pro
                85                  90                  95

Tyr Thr Phe Gly Gln Gly Thr Lys Leu Glu Ile Arg
            100                 105


<210> SEQ ID NO 48
<211> LENGTH: 107
<212> TYPE: PRT
<213> ORGANISM: Artificial Sequence
<220> FEATURE:
<223> OTHER INFORMATION: VL for A5G9C2C7

<400> SEQUENCE: 48

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Asn Ile Tyr Asn Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Asn Ser Arg
                85                  90                  95
```

```
Thr Phe Gly Gln Gly Thr Lys Val Glu Ile Lys
            100                 105


<210> SEQ ID NO 49
<211> LENGTH: 330
<212> TYPE: PRT
<213> ORGANISM: Artificial Sequence
<220> FEATURE:
<223> OTHER INFORMATION: Heavy chain constant region

<400> SEQUENCE: 49

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 50
<211> LENGTH: 107
```

<212> TYPE: PRT
<213> ORGANISM: Artificial Sequence
<220> FEATURE:
<223> OTHER INFORMATION: Light chain constant region

<400> SEQUENCE: 50

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 51
<211> LENGTH: 448
<212> TYPE: PRT
<213> ORGANISM: Artificial Sequence
<220> FEATURE:
<223> OTHER INFORMATION: Heavy chain of Eculizumab

<400> SEQUENCE: 51

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220
```

```
Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445


<210> SEQ ID NO 52
<211> LENGTH: 200
<212> TYPE: PRT
<213> ORGANISM: Artificial Sequence
<220> FEATURE:
<223> OTHER INFORMATION: Light chain of Eculizumab

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly
        195                 200


<210> SEQ ID NO 53
<211> LENGTH: 447
<212> TYPE: PRT
<213> ORGANISM: Artificial Sequence
<220> FEATURE:
<223> OTHER INFORMATION: Heavy chain of Ravulizumab

<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300
```

```
Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Leu His Glu Ala
            420                 425                 430

Leu His Ser His Tyr Thr Gln Lys Ser Leu Ser Leu Ser Leu Gly
        435                 440                 445


<210> SEQ ID NO 54
<211> LENGTH: 214
<212> TYPE: PRT
<213> ORGANISM: Artificial Sequence
<220> FEATURE:
<223> OTHER INFORMATION: Light chain of Ravulizumab

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 55
<211> LENGTH: 451
<212> TYPE: PRT
<213> ORGANISM: Artificial Sequence
<220> FEATURE:
<223> OTHER INFORMATION: Heavy chain of Crovalimab

<400> SEQUENCE: 55

```
Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val His Ser Ser
            20                  25                  30

Tyr Tyr Met Ala Trp Val Arg Gln Ala Pro Gly Lys Gly Leu Glu Trp
        35                  40                  45

Val Gly Ala Ile Phe Thr Gly Ser Gly Ala Glu Tyr Lys Ala Glu Trp
    50                  55                  60

Ala Lys Gly Arg Val Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Ser Asp Ala Gly Tyr Asp Tyr Pro Thr His Ala Met His Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Arg Arg Gly Pro Lys Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365
```

```
Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Leu His Glu Ala Leu His Ala His Tyr Thr Arg Lys Glu Leu Ser
        435                 440                 445

Leu Ser Pro
    450


<210> SEQ ID NO 56
<211> LENGTH: 217
<212> TYPE: PRT
<213> ORGANISM: Artificial Sequence
<220> FEATURE:
<223> OTHER INFORMATION: Light chain of Crovalimab

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ser
            20                  25                  30

Leu Ala Trp Tyr Gln Gln Lys Pro Gly Lys Ala Pro Lys Leu Leu Ile
        35                  40                  45

Tyr Gly Ala Ser Glu Thr Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Thr Lys Val Gly Ser Ser
                85                  90                  95

Tyr Gly Asn Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 57
<211> LENGTH: 447
<212> TYPE: PRT
<213> ORGANISM: Artificial Sequence
<220> FEATURE:
<223> OTHER INFORMATION: Heavy chain of Pozelimab
```

<400> SEQUENCE: 57

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Val Ser Ser Ser
            20                  25                  30

Tyr Trp Thr Trp Ile Arg Gln Pro Pro Gly Lys Gly Leu Glu Trp Ile
        35                  40                  45

Gly Tyr Ile Tyr Tyr Ser Gly Ser Ser Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Asn Val Asp Thr Thr Met Ile Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415
```

```
Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 58
<211> LENGTH: 214
<212> TYPE: PRT
<213> ORGANISM: Artificial Sequence
<220> FEATURE:
<223> OTHER INFORMATION: Light chain of Pozelimab

<400> SEQUENCE: 58

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ala Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 59
<211> LENGTH: 107
<212> TYPE: PRT
<213> ORGANISM: Artificial Sequence
<220> FEATURE:
<223> OTHER INFORMATION: VL for A5G2A1A1

<400> SEQUENCE: 59

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asp Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
```

-continued

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Asn Asn Phe Pro Trp
                85                  90                  95

Thr Phe Gly Gln Gly Thr Lys Val Asp Phe Lys
            100                 105
```

ANTIBODIES BINDING C5 AND USES THEREOF

RELATED APPLICATIONS AND INCORPORATION BY REFERENCE

This application claims priority to U.S. provisional patent application Ser. No. 63/051,966 filed on Jul. 15, 2020.

The foregoing application, all documents cited therein or during its prosecution ("appln cited documents") and all documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any Genbank sequences mentioned in this disclosure are incorporated by reference with the Genbank sequence to be that of the earliest effective filing date of this disclosure.

SEQUENCE STATEMENT

The instant application contains a Sequence Listing which has been submitted electronically and is hereby incorporated by reference in its entirety. Said ASCII copy was created Jul. 15, 2021, is named 55532_00092SL.txt and is 49,464 bytes in size.

FIELD OF THE INVENTION

The present disclosure relates generally to an isolated monoclonal antibody, particularly a human monoclonal antibody, or an antigen-binding portion thereof, that binds to human C5, with high affinity and functionality. A nucleic acid molecule encoding the antibody or the antigen-binding portion thereof, an expression vector, a host cell and a method for expressing the antibody or the antigen-binding portion thereof are also provided. The present disclosure further provides a bispecific molecule, an immunoconjugate, a chimeric antigen receptor, an oncolytic virus, and a pharmaceutical composition which may comprise the antibody or the antigen-binding portion thereof, as well as a treatment method using the anti-C5 antibody or antigen-binding portion thereof of the disclosure.

BACKGROUND OF THE INVENTION

The complement system is part of the innate immune system that consists of plasma proteins mainly produced by the liver. These complement proteins react with one another to opsonize pathogens and induce a series of inflammatory responses to help fight infection.

The complement system activation may be initiated by three pathways, the classical, lectin and alternative pathways, depending on the context, which lead to a common terminal pathway where the complement component 5 (C5) is cleaved by the C5 convertase into C5a and C5b fragments (Merle N S et al. (2015) *Front Immunol.* 6:262). The C5a fragment triggers the inflammatory response, recruiting phagocytes to infection site and activating leukocytes, endothelial cells or platelets. The C5b fragment recruits and polymerizes with complement components C6-C9 to form the membrane attack complex (MAC) which generates large pores on the cell membrane of target cells, such as metabolically inert cells and Gram-negative bacteria, and induces cell lysis (Koski C L et al., (1983) *Proc Natl Acad Sci USA* 80:3816-3820: Lewis L A and Ram S (2014) *Virulence* 5:98-126). For Gram-positive bacteria and metabolically active cells that are resistant to complement mediated lysis, multiple MACs are inserted to the target cells to induce calcium flux and subsequence apoptosis (Cole D S, and Morgan B P. (2003) *Clin Sci* 1979 (104): 455-66). C5 may also be cleaved by thrombin at another site as compared to the C5 convertase to generate intermediates C5T and C5bT, independently of the complement system. These intermediates are converted into C5a and C5b upon activation of the coagulation cascade (Merle N S et al., (2015) supra).

To avoid complement activation in non-infected areas and the resulting damage to healthy tissues, host cells express multiple regulatory proteins on the cell membranes (Schmidt C Q et al., (2016) *Immunol Rev.* (2016) 274 (2): 152-171). Apoptotic cells with reduced regulators induce complement activation at a low level and are rapidly cleared by phagocytes (Verbovetski I et al., (2002) *J Exp Med* 196:1553-1561). The lack of MAC inhibitor CD59 due to genetic deficiency may lead to erythrocyte destruction, causing paroxysmal nocturnal hemoglobinuria (PNH) (Holguin M H et al., (1989) *J Clin Invest* 84:1387-1394). In addition to PNH, dysregulation of the complement system is also implicated in the pathogenesis of other hemolytic disorders, such as atypical hemolytic uremic syndrome (aHUS), which is associated with C3 convertase mutation, and inflammatory diseases, such as Myasthenia Gravis where MAC formation is confirmed to be responsible for the disrupted neurotransmission at the neuromuscular junction, and neuromyelitis optica spectrum disorder (NMOSD) characterized by immune-mediated demyelination and axonal damage.

C5 inhibitors have been developed to target excessive C5a production and/or MAC formation. For example, eculizumab, a long-acting humanized monoclonal antibody that inhibits the cleavage of C5 into C5a and C5b, has been clinically approved for treatment of PNH, aHUS, generalized Myasthenia Gravis (gMG), and NMOSD, and is in clinical trials for HELLP syndrome, COVID-19 and etc. Ravulizumab is an eculizumab like antibody having a longer half-life and has been approved to treat PNH and aHUS.

One major problem associated with eculizumab treatment is the reduced level or even lack of MACs for bacteria destruction and also reduced level or lack of C5a-dependent activation of phagocytic cells, resulting in increased risk of developing a meningococcal disease (McNamara L A et al., (2017) *Am J Transplant* 17:2481-2484; Konar M et al., (2017) *Blood* 130:891-899). An anti-C5 single domain antibody functionally mimicking the C-terminal domain of the *Staphylococcus aureus* SSL7 protein has been reported to inhibit MAC assembly on host cells while maintaining the bactericidal activity. The low affinity of this antibody to C5 precludes its further evaluation in animal models, but antibodies with similar selective inhibitory effects may be the target in future screening (Yatime L et al., (2018) *Front Immunol.* 9:2822). Another problem with eculizumab is the C5 mutation such as R885C in certain PNH patients that leads to poor response to eculizumab (Nishimura J et al., (2014) *N ENGL J MED* 370 (7): 632-639). Antibodies binding to different C5 epitopes are always needed for patients carrying such C5 mutations.

Citation or identification of any document in this application is not an admission that such document is available as prior art to the present invention.

SUMMARY OF THE INVENTION

The present disclosure provides an isolated human monoclonal antibody, or an antigen-binding portion thereof, that binds to C5 (e.g., the human C5, including the wild-type C5 and the C5 variant carrying R885H mutation) and has comparable, if not higher, binding affinity/capacity to human and/or monkey C5, and comparable, if not higher, inhibitory effects on C5 cleavage into C5a and C5b and the subsequent complement-mediated hemolysis and/or inflammation, as compared to prior art anti-C5 antibodies such as eculizumab.

The antibody or antigen-binding portion thereof of the disclosure can be used for a variety of applications, including detection of C5 proteins, and treatment and prevention of diseases associated with excessive C5a and/or C5b production, such as hemolytic disorders and inflammatory diseases.

Accordingly, in one aspect, the disclosure pertains to an isolated human monoclonal antibody, or an antigen-binding portion thereof, that binds C5, having (i) a heavy chain variable region that may comprise a VH CDR1 region, a VH CDR2 region and a VH CDR3 region, wherein the VH CDR1 region, the VH CDR2 region and the VH CDR3 region may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 1, 7 and 14, respectively; (2) SEQ ID NOs: 2, 8 and 15, respectively; (3) SEQ ID NOs: 2, 8 and 16, respectively; (4) SEQ ID NOs: 3, 9 and 17, respectively; (5) SEQ ID NOs: 4, 10 and 18, respectively; (6) SEQ ID NOs: 4, 11 and 18, respectively; (7) SEQ ID NOs: 4, 12 and 18, respectively; (8) SEQ ID NOs: 5, 12 and 18, respectively; or (9) SEQ ID NOs: 6, 13 and 19, respectively; and/or (ii) a light chain variable region that may comprise a VL CDR1 region, a VL CDR2 region and a VL CDR3 region, wherein the VL CDR1 region, the VL CDR2 region and the VL CDR3 region may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 20, 25 and 31, respectively; (2) SEQ ID NOs: 20, 26 and 32, respectively; (3) SEQ ID NOs: 20, 25 and 33, respectively; (4) SEQ ID NOs: 21, 27 and 34, respectively; (5) SEQ ID NOs: 22, 28 and 35, respectively; (6) SEQ ID NOs: 23, 29 and 36, respectively; or (7) SEQ ID NOs: 24, 30 and 37, respectively.

The isolated monoclonal antibody, or the antigen-binding portion thereof, of the present disclosure may comprise a heavy chain variable region having a VH CDR1 region, a VH CDR2 region and a VH CDR3 region, and a light chain variable region having a VL CDR1 region, a VL CDR2 region and a VL CDR3 region, wherein the VH CDR1, VH CDR2, VH CDR3, VL CDR1, VL CDR2 and VL CDR3 may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 1, 7, 14, 20, 25 and 31, respectively; (2) SEQ ID NOs: 2, 8, 15, 20, 26 and 32, respectively; (3) SEQ ID NOs: 2, 8, 16, 20, 25 and 33, respectively; (4) SEQ ID NOs: 3, 9, 17, 21, 27 and 34, respectively; (5) SEQ ID NOs: 4, 10, 18, 22, 28 and 35, respectively; (6) SEQ ID NOs: 4, 11, 18, 22, 28 and 35, respectively; (7) SEQ ID NOs: 4, 12, 18, 23, 29 and 36, respectively; (8) SEQ ID NOs: 5, 12, 18, 23, 29 and 36, respectively; or (9) SEQ ID NOs: 6, 13, 19, 24, 30 and 37, respectively.

The isolated monoclonal antibody, or the antigen-binding portion thereof, of the present disclosure may comprise a heavy chain variable region that may comprise an amino acid sequence having at least 85%, 86%, 87%, 88%, 89%, 90%, 91%, 92%, 93%, 94%, 95%, 96%, 97%, 98%, 99% or 100% identity to SEQ ID NOs: 38, 39 (X1=I, X2=I, X3=S, X4=F; X1=L, X2=M, X3=G, X4=L), 40, 41 (X1=T, X2=N; X1=S, X2=F), 42 (X1=R; X1=K) or 43.

The isolated monoclonal antibody, or the antigen-binding portion thereof, of the present disclosure may comprise a light chain variable region that may comprise an amino acid sequence having at least 85%, 86%, 87%, 88%, 89%, 90%, 91%, 92%, 93%, 94%, 95%, 96%, 97%, 98%, 99% or 100% identity to SEQ ID NOs: 44 (X1=S, X2=S, X3=F; X1=T, X2=H, X3=I), 45, 46, 47, 48, or 59.

The isolated monoclonal antibody, or the antigen-binding portion thereof, of the present disclosure may comprise a heavy chain variable region and a light chain variable region, the heavy chain variable region and the light chain variable region may comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 38 and 44 (X1=S, X2=S, X3=F), respectively; (2) SEQ ID NOs: 39 (X1=I, X2=I, X3=S, X4=F) and 59, respectively; (3) SEQ ID NOs: 39 (X1=L, X2=M, X3=G, X4=L) and 44 (X1=T, X2=H, X3=I), respectively; (4) SEQ ID NOs: 40 and 45, respectively; (5) SEQ ID NOs: 41 (X1=T, X2=N) and 46, respectively; (6) SEQ ID NOs: 41 (X1=S, X2=F) and 46, respectively; (7) SEQ ID NOs: 42 (X1=R) and 47, respectively; (8) SEQ ID NOs: 42 (X1=K) and 47, respectively; or (9) SEQ ID NOs: 43 and 48, respectively.

The isolated monoclonal antibody, or the antigen-binding portion thereof, of the present disclosure may comprise a heavy chain and a light chain linked by disulfide bonds, the heavy chain may comprise a heavy chain variable region and a heavy chain constant region, the light chain may comprise a light chain variable region and a light chain constant region, wherein the C terminus of the heavy chain variable region is linked to the N terminus of the heavy chain constant region, and the C terminus of the light chain variable region is linked to the N terminus of the light chain constant region, wherein the heavy chain variable region and the light chain variable region may comprise amino acid sequences described above, and the antibody or antigen-binding portion thereof binds to C5. The heavy chain constant region may be human IgG1 constant region having an amino acid sequence set forth in e.g., SEQ ID NO.: 49, and the light chain constant region may be human kappa constant region having an amino acid sequences set forth in e.g., SEQ ID NO.: 50. The heavy chain constant region may also be human IgG2 or IgG4 constant region, and the light chain constant region may be human lambda constant region.

The antibody of the present disclosure in some embodiments may comprise or consist of two heavy chains and two light chains, wherein each heavy chain may comprise the heavy chain constant region, heavy chain variable region or CDR sequences mentioned above, and each light chain may comprise the light chain constant region, light chain variable region or CDR sequences mentioned above, wherein the antibody binds to C5. The antibody of the disclosure can be a full-length antibody, for example, of an IgG1, IgG2 or IgG4 isotype. The antibody or the antigen-binding portion thereof of the present disclosure in other embodiments may be a single chain variable fragment (scFv) antibody, or antibody fragments, such as Fab or F (ab), fragments.

The disclosure also provides a bispecific molecule that may comprise the antibody, or the antigen-binding portion thereof, of the disclosure, linked to a second functional moiety (e.g., a second antibody) having a different binding specificity than said antibody, or antigen-binding portion thereof. The disclosure also provides an immunoconjugate, such as an antibody-drug conjugate, that may comprise an antibody, or antigen-binding portion thereof, of the disclosure, linked to a therapeutic agent, such as a cytotoxin. In another aspect, the antibody or the antigen binding portion thereof of the present disclosure can be made into part of a chimeric antigen receptor (CAR). Also provided is an immune cell that may comprise the antigen chimeric receptor, such as a T cell and a NK cell. The antibody or the antigen binding portion thereof of the present disclosure can also be encoded by or used in conjunction with an oncolytic virus.

Nucleic acid molecules encoding the antibody, or the antigen-binding portion thereof, of the disclosure are also encompassed by the disclosure, as well as expression vectors that may comprise such nucleic acids and host cells that may comprise such expression vectors. A method for preparing the anti-C5 antibody or the antigen-binding portion thereof of the disclosure using the host cell is also provided, that may comprise steps of (i) expressing the antibody in the host cell and (ii) isolating the antibody from the host cell or its cell culture.

Compositions that may comprise the antibody, or the antigen-binding portion thereof, or the immunoconjugate, the bispecific molecule, the oncolytic virus, the immune cell with CAR, the nucleic acid molecule, or the expression vector of the disclosure, and a pharmaceutically acceptable carrier, arc also provided. In certain embodiments, the pharmaceutical composition may further contain a therapeutic agent for treating a specific disease, such as an anti-inflammatory agent.

In yet another aspect, the disclosure provides a method for treating a disease associated with excessive C5a and/or C5b production, which may comprise administering to a subject a therapeutically effective amount of the composition of the present disclosure.

The disease may be a complement-mediated hemolytic disorder. The hemolytic disorder tumor includes, but not limited to, PNH and aHUS. In certain embodiments, the method for treating the hemolytic disorder may comprise administering an antibody or an antigen-binding portion thereof of the disclosure, or alternatively a nucleic acid molecule or a vector of the disclosure capable of expressing the same in the subject. In certain embodiments, the subject is human.

The disease may be a complement-mediated inflammatory disease, such as an autoimmune disease. The inflammatory disease includes, but not limited to, gMG and NMOSD. In certain embodiments, the method for treating the hemolytic disorder may comprise administering an antibody or an antigen-binding portion thereof of the disclosure, or alternatively a nucleic acid molecule or a vector of the disclosure capable of expressing the same in the subject. In certain embodiments, the subject having gMG may be further administered with prednisone. In certain embodiments, the subject with NMOSD is further administered with azathioprine. In certain embodiments, the subject is human.

Other features and advantages of the instant disclosure will be apparent from the following detailed description and examples, which should not be construed as limiting. The contents of all references. Genbank entries, patents and published patent applications cited throughout this application are expressly incorporated herein by reference.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53 (c) EPC and Rule 28 (b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1A:
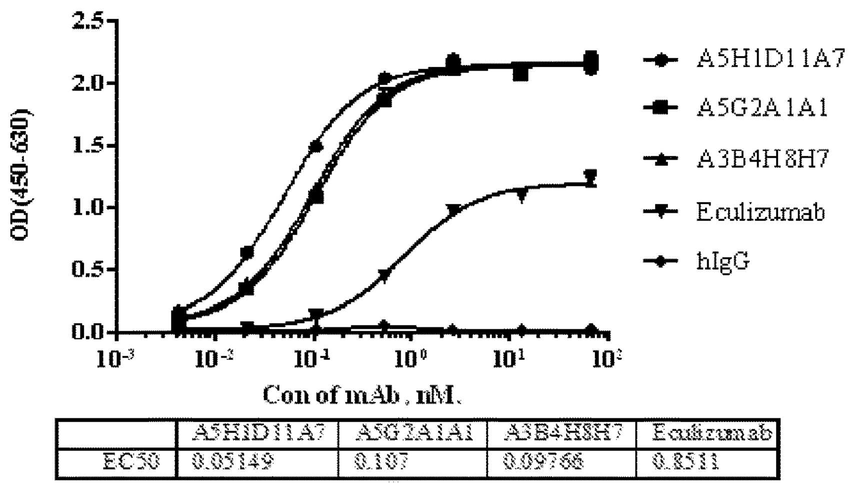
FIGS. 1A-IC show the binding capacities of antibodies A5H1D11A7, A5G2A1A1 and A3B4H8H7 (A), A2E12G12H7 and A5F3D5A1 (B), A4G10B7A7, A3C8E4H1, A6A1H9B7 and A5G9C2C7 (C) to human C5 in a capture ELISA.

To ensure that the present disclosure may be more readily understood, certain terms are first defined. Additional definitions are set forth throughout the detailed description.

The term "C5" refers to complement component 5. The term "C5" may comprise variants, isoforms, homologs, orthologs and paralogs. For example, an antibody specific for a human C5 protein may, in certain cases, cross-react with a C5 protein from a species other than human, such as monkey. In other embodiments, an antibody specific for a human C5 protein may be completely specific for the human C5 protein and exhibit no cross-reactivity to other species or of other types, or may cross-react with C5 from certain other species but not all other species.

The term "human C5" refers to a C5 protein having an amino acid sequence from a human, such as the amino acid sequence of human C5 having a Genbank accession number of AAI13739.1. The human C5 protein may contain a mutation at the 885th amino acid residue. The terms "monkey C5" or "cynomolgus C5" refer to a C5 protein having an amino acid sequence from *Macaca fascicularis*, such as the amino acid sequence having NCBI Reference No. XP_005580972.1.

The term "antibody" as referred to herein includes whole antibodies and any antigen binding fragment (i.e., "antigen-binding portion") or single chains thereof. Whole antibodies are glycoproteins which may comprise two heavy (H) chains and two light (L) chains inter-connected by disulfide bonds. Each heavy chain may be comprised of a heavy chain variable region (abbreviated herein as $V_H$) and a heavy chain constant region. The heavy chain constant region may be comprised of three domains, $C_{H1}$, $C_{H2}$ and $C_{H3}$. Each light chain may be comprised of a light chain variable region (abbreviated herein as $V_L$) and a light chain constant region. The light chain constant region may be comprised of one domain. $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., a C5 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a $F(ab')_2$ fragment, a bivalent fragment which may comprise two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR); and (viii) a nanobody, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a C5 protein is substantially free of antibodies that specifically bind antigens other than C5 proteins). An isolated antibody that specifically binds a human C5 protein may, however, have cross-reactivity to other antigens, such as C5 proteins from other species. Moreover, an isolated antibody can be substantially free of other cellular material and/or chemicals.

The term "monoclonal antibody" as used herein refers to an antibody obtained from a population of substantially homogenous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species have been grafted onto human framework sequences.

The term "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen".

As used herein, an antibody that "specifically binds to human C5" is intended to refer to an antibody that binds to human C5 protein (and possibly a C5 protein from one or more non-human species) but does not substantially bind to non-C5 proteins. Preferably, the antibody binds to human C5 protein with "high affinity", namely with a $K_D$ of $5.0\times10^{-8}$ M or less, more preferably $2.0\times10^{-9}$ M or less, and more preferably $1.0\times10^{-9}$ M or less.

The term "does not substantially bind" to a protein or cells, as used herein, means does not bind or does not bind with a high affinity to the protein or cells, i.e. binds to the protein or cells with a $K_D$ of $1.0\times10^{-6}$ M or more, more preferably $1.0\times10^{-5}$ M or more, more preferably $1.0\times10^{-4}$ M or more, more preferably $1.0\times10^{-3}$ M or more, even more preferably $1.0\times10^{-2}$ M or more.

The term "high affinity" for an IgG antibody refers to an antibody having a $K_D$ of $1.0\times10^{-6}$ M or less, more preferably $5.0\times10^{-8}$ M or less, even more preferably $3.0\times10^{-8}$ M or less, even more preferably $2.0\times10^{-9}$ M or less and even more preferably $1.0\times10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore™ system.

The term "$EC_{50}$", also known as half maximal effective concentration, refers to the concentration of an antibody which induces a response halfway between the baseline and maximum after a specified exposure time.

The term "$IC_{50}$", also known as half maximal inhibitory concentration, refers to the concentration of an antibody which inhibits a specific biological or biochemical function by 50% relative to the absence of the antibody.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "therapeutically effective amount" means an amount of the antibody of the present disclosure sufficient to prevent or ameliorate the symptoms associated with a disease or condition (such as a hemolytic disorder) and/or lessen the severity of the disease or condition. A therapeutically effective amount is understood to be in context to the condition being treated, where the actual effective amount is readily discerned by those of skill in the art.

Various aspects of the disclosure are described in further detail in the following subsections.

The antibody, or the antigen-binding portion thereof, of the disclosure specifically may bind to human C5 with comparable, if not better, binding affinity/capacity as compared to previously described anti-C5 antibodies, such as eculizumab.

The antibody, or the antigen-binding portion thereof, of the disclosure may inhibit C5 cleavage into C5a and C5b and thus the complement-mediated inflammation and/or hemolysis, with comparable or higher activity, as compared to previously described anti-C5 antibodies, such as eculizumab.

The antibodies of the disclosure are human monoclonal antibodies.

The antibody or antigen-binding portion thereof of the disclosure is structurally and chemically characterized as described below and in the following Examples. The amino acid sequence ID numbers of the heavy/light chain variable regions of the antibodies are summarized in Table I above, some antibodies sharing the same $V_H$ or $V_L$. The heavy chain constant region for the antibodies may be human IgG1 heavy chain constant region having an amino acid sequence set forth in, e.g., SEQ ID NO: 49, and the light chain constant region for the antibodies may be human kappa constant region having an amino acid sequence set forth in, e.g., SEQ ID NO: 50. The antibodies of the disclosure may also contain human IgG4 heavy chain constant region and human lambda light chain constant region.

The heavy chain variable region CDRs and the light chain variable region CDRs in Table 1 have been defined by the Kabat numbering system. However, as is well known in the art. CDR regions can also be determined by other systems such as Chothia, and IMGT, AbM, or Contact numbering system/method, based on heavy chain/light chain variable region sequences.

The $V_H$ and $V_L$ sequences (or CDR sequences) of other anti-C5 antibodies which bind to human C5 can be "mixed and matched" with the $V_H$ and $V_L$ sequences (or CDR sequences) of the anti-C5 antibody of the present disclosure. Preferably, when $V_H$ and $V_L$ chains (or the CDRs within such chains) are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one embodiment, an antibody of the disclosure, or an antigen binding portion thereof, may comprise:

(a) a heavy chain variable region which may comprise an amino acid sequence listed above in Table 1; and (b) a light chain variable region which may comprise an amino acid sequence listed above in Table 1, or the $V_L$ of another anti-C5 antibody, wherein the antibody specifically binds human C5.

In another embodiment, an antibody of the disclosure, or an antigen binding portion thereof, may comprise:

(a) the CDR1, CDR2, and CDR3 regions of the heavy chain variable region listed above in Table 1; and (b) the CDR1, CDR2, and CDR3 regions of the light chain variable region listed above in Table 1 or the CDRs of another anti-C5 antibody, wherein the antibody specifically binds human C5.

| mAb ID | VH-CDR1 (SEQ ID NO.) | VH-CDR2 (SEQ ID NO.) | VH-CDR3 (SEQ ID NO.) | VH (SEQ ID NO.) | VL-CDR1 (SEQ ID NO.) | VL-CDR2 (SEQ ID NO.) | VL-CDR3 (SEQ ID NO.) | VL (SEQ ID NO.) |
|---|---|---|---|---|---|---|---|---|
| A5H1D11A7 | 1 | 7 | 14 | 38 | 20 | 25 | 31 | 44, X1 = S, X2 = S, X3 = F |
| A5G2A1A1 | 2 | 8 | 15 | 39, X1 = I, X2 = I, X3 = S, X4 = F | 20 | 26 | 32 | 59 |
| A3C8E4H1 | 2 | 8 | 16 | 39, X1 = L, X2 = M, X3 = G, X4 = L | 20 | 25 | 33 | 44, X1 = T, X2 = H, X3 = I |
| A2E12G12H7 | 3 | 9 | 17 | 40 | 21 | 27 | 34 | 45 |
| A3B4H8H7 | 4 | 10 | 18 | 41, X1 = T, X2 = N | 22 | 28 | 35 | 46 |
| A6A1H9B7 | 4 | 11 | 18 | 41, X1 = S, X2 = F | 22 | 28 | 35 | 46 |
| A4G10B7A7 | 4 | 12 | 18 | 42, X1 = R | 23 | 29 | 36 | 47 |
| A5F3D5A1 | 5 | 12 | 18 | 42, X1 = K | 23 | 29 | 36 | 47 |
| A5G9C2C7 | 6 | 13 | 19 | 43 | 24 | 30 | 37 | 48 |

In yet another embodiment, the antibody, or antigen binding portion thereof, includes the heavy chain variable CDR2 region of anti-C5 antibody combined with CDRs of other antibodies which bind human C5, e.g., CDR1 and/or CDR3 from the heavy chain variable region, and/or CDR1, CDR2, and/or CDR3 from the light chain variable region of a different anti-C5 antibody.

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *British J, of Cancer* 83 (2): 252-260 (2000); Beiboer et al., *J. Mol. Biol.* 296:833-849 (2000); Rader et al., *Proc. Natl. Acad. Sci. U.S.A.* 95:8910-8915 (1998); Barbas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157:739-749 (1996): Berezov et al., *BIAjournal* 8: Scientific Review 8 (2001); Igarashi et al., *J. Biochem* (Tokyo) 117:452-7 (1995): Bourgeois et al., *J. Virol* 72:807-10 (1998); Levi et al., *Proc. Natl. Acad. Sci. U.S.A.* 90:4374-8 (1993); Polymenis and Stoller, *J. Immunol.* 152: 5218-5329 (1994) and Xu and Davis. Immunity 13:37-45 (2000). See also U.S. Pat. Nos. 6,951,646; 6,914,128; 6,090, 382; 6,818,216; 6,156,313; 6,827,925; 5,833,943; 5,762,905 and 5,760,185. Each of these references is hereby incorporated by reference in its entirety.

Accordingly, in another embodiment, antibodies of the disclosure may comprise the CDR2 of the heavy chain variable region of the anti-C5 antibody and at least the CDR3 of the heavy and/or light chain variable region of the anti-C5 antibody, or the CDR3 of the heavy and/or light chain variable region of another anti-C5 antibody, wherein the antibody is capable of specifically binding to human C5. These antibodies preferably (a) compete for binding with C5; (b) retain the functional characteristics; (c) bind to the same epitope; and/or (d) have a similar binding affinity as the anti-C5 antibody of the present disclosure. In yet another embodiment, the antibodies further may comprise the CDR2 of the light chain variable region of the anti-C5 antibody, or the CDR2 of the light chain variable region of another anti-C5 antibody, wherein the antibody is capable of specifically binding to human C5. In another embodiment, the antibodies of the disclosure may include the CDR1 of the heavy and/or light chain variable region of the anti-C5 antibody, or the CDR1 of the heavy and/or light chain variable region of another anti-C5 antibody, wherein the antibody is capable of specifically binding to human C5.

In another embodiment, an antibody of the disclosure may comprise a heavy and/or light chain variable region sequences of CDR1, CDR2 and CDR3 sequences which differ from those of the anti-C5 antibodies of the present disclosure by one or more conservative modifications. It is understood in the art that certain conservative sequence modification can be made which do not remove antigen binding. Sec, e.g., Brummell et al., (1993) *Biochem* 32:1180-8; de Wildt et al., (1997) *Prot. Eng.* 10:835-41; Komissarov et al., (1997) *J. Biol. Chem.* 272:26864-26870; Hall et al., (1992) *J. Immunol.* 149:1605-12; Kelley and O'Connell (1993) *Biochem.* 32:6862-35; Adib-Conquy et al., (1998) *Int. Immunol.* 10:341-6 and Beers et al., (2000) *Clin. Can. Res.* 6:2835-43.

Accordingly, in one embodiment, the antibody may comprise a heavy chain variable region which may comprise CDR1, CDR2, and CDR3 sequences and/or a light chain variable region which may comprise CDR1, CDR2, and CDR3 sequences, wherein:

(a) the heavy chain variable region CDR1 sequence may comprise a sequence listed in Table 1 above, and/or conservative modifications thereof; and/or (b) the heavy chain variable region CDR2 sequence may comprise a sequence listed in Table 1 above, and/or conservative modifications thereof; and/or (c) the heavy chain variable region CDR3 sequence may comprise a sequence listed in Table I above, and conservative modifications thereof; and/or (d) the light chain variable region CDR1, and/or CDR2, and/or CDR3 sequences may comprise the sequence(s) listed in Table I above; and/or conservative modifications thereof; and (e) the antibody specifically binds human C5.

The antibody of the present disclosure possesses one or more of the following functional properties described above, such as high affinity binding to human C5, and blocking activity on C5-IL6 binding.

In various embodiments, the antibody can be, for example, a mouse, human, humanized or chimeric antibody.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the disclosure can be replaced with other amino acid residues from the same side chain family and the altered antibody can be tested for retained function (i.e., the functions set forth above) using the functional assays described herein.

Antibodies of the disclosure can be prepared using an antibody having one or more of the $V_H/V_L$ sequences of the anti-C5 antibody of the present disclosure as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function (s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Ricchmann et al., (1998) *Nature* 332:323-327; Jones et al., (1986) *Nature* 321:522-525: Queen et al., (1989) *Proc. Natl. Acad*. See also U.S.A. 86:10029-10033: U.S. Pat. Nos. 5,225,539; 5,530,101; 5,585,089; 5,693,762 and 6,180,370).

Accordingly, another embodiment of the disclosure pertains to an isolated monoclonal antibody, or antigen binding portion thereof, which may comprise a heavy chain variable region that may comprise CDR1, CDR2, and CDR3 sequences which may comprise the sequences of the present disclosure, as described above, and/or a light chain variable region which may comprise CDR1, CDR2, and CDR3 sequences which may comprise the sequences of the present disclosure, as described above. While these antibodies contain the $V_H$ and $V_L$ CDR sequences of the monoclonal antibody of the present disclosure, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al., (1991), cited supra: Tomlinson et al., (1992) *J. Mol. Biol.* 227:776-798; and Cox et al., (1994) *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG—0010109, NT—024637 & BC070333), 3-33 (NG—0010109 & NT—024637) and 3-7 (NG—0010109 & NT—024637). As another example, the following heavy chain germline sequences found in the HCo12 HuMAb mouse are available in the accompanying Genbank Accession Nos.: 1-69 (NG—0010109, NT—024637 & BC070333), 5-51 (NG—0010109 & NT—024637), 4-34 (NG—0010109 & NT—024637), 3-30.3 (CAJ556644) & 3-23 (AJ406678).

Antibody protein sequences are compared against a compiled protein sequence database using one of the sequence similarity searching methods called the Gapped BLAST (Altschul et al., (1997), supra), which is well known to those skilled in the art.

Preferred framework sequences for use in the antibodies of the disclosure are those that are structurally similar to the framework sequences used by antibodies of the disclosure. The $V_H$ CDR1. CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Accordingly, in another embodiment, the disclosure provides isolated anti-C5 monoclonal antibodies, or antigen binding portions thereof, which may comprise a heavy chain variable region that may comprise: (a) a $V_H$ CDR1 region which may comprise the sequence of the present disclosure, or an amino acid sequence having one, two, three, four or five amino acid substitutions, deletions or additions; (b) a $V_H$ CDR2 region which may comprise the sequence of the present disclosure, or an amino acid sequence having one, two, three, four or five amino acid substitutions, deletions or additions; (c) a $V_H$ CDR3 region which may comprise the sequence of the present disclosure, or an amino acid sequence having one, two, three, four or five amino acid substitutions, deletions or additions; (d) a $V_L$ CDR1 region which may comprise the sequence of the present disclosure, or an amino acid sequence having one, two, three, four or five amino acid substitutions, deletions or additions; (e) a $V_L$ CDR2 region which may comprise the sequence of the present disclosure, or an amino acid sequence having one, two, three, four or five amino acid substitutions, deletions or additions; and (f) a $V_L$ CDR3 region which may comprise the sequence of the present disclosure, or an amino acid sequence having one, two, three, four or five amino acid substitutions, deletions or additions.

Engineered antibodies of the disclosure include those in which modifications have been made to framework residues within $V_H$ and/or $V_L$, e.g. to improve the properties of the antibody. Typically, such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition, or as an alternative to modifications made within the framework or CDR regions, antibodies of the disclosure can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure can be chemically modified (e.g., one or more chemical moieties can be attached to the antibody) or be modified to alter its glycosylation, again to alter one or more functional properties of the antibody.

In one embodiment, the hinge region of $C_{H1}$ is modified in such that the number of cysteine residues in the hinge region is altered, e.g., increased or decreased. This approach is described further in U.S. Pat. No. 5,677,425. The number of cysteine residues in the hinge region of $C_{H1}$ is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the $C_{H2}$-$C_{H3}$ domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase or reduce the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, the cell lines Ms704, Ms705, and Ms709 lack the fucosyltransferase gene, FUT8 ($\alpha$(1, 6)-fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see U.S. Patent Publication No. 20040110704 and Yamane-Ohnuki et al., (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the $\alpha$-1, 6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line. Lec13 cells, with reduced ability to attach fucose to Asn(297)-linked carbohydrates, also resulting in hypofucosylation of antibodies expressed in that host cell (see also Shields et al., (2002) J. Biol. Chem. 277:26733-26740). Antibodies with a modified glycosylation profile can also be produced in chicken eggs, as described in PCT Publication WO 06/089231. Alternatively, antibodies with a modified glycosylation profile can be produced in plant cells, such as *Lemna*. Methods for production of antibodies in a plant system are disclosed in the U.S. patent application corresponding to Alston & Bird LLP Ser. No. 60/836,998, filed on Aug. 11, 2006. The fucose residues of the antibody can be cleaved off using a fucosidase enzyme; e.g., the fucosidase a-L-fucosidase removes fucosyl residues from antibodies (Tarentino et al., (1975) *Biochem.* 14:5516-23).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See, e.g., EP 0 154 316 and EP 0 401 384.

Antibodies of the disclosure can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12: 43R-56R; Parekh et al (1985) *Nature* 316:452-7; Mimura et al., (2000) *Mol Immunol* 37:697-706). Glycosylation has been known to occur at motifs containing an N-X-S/T sequence. In some instances, it is preferred to have an anti-C5 antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a link into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-C5 antibody that contains a pI value that falls in the normal range. This can be achieved either by selecting antibodies with a pI in the normal range or by mutating charged surface residues.

In another aspect, the disclosure provides nucleic acid molecules that encode heavy and/or light chain variable regions, or CDRs, of the antibodies of the disclosure. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the disclosure can be, e.g., DNA or RNA and may or may not contain intronic sequences. In a preferred embodiment, the nucleic acid is a cDNA molecule.

Nucleic acids of the disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the disclosure include those encoding the $V_H$ and $V_L$ sequences of the C5 monoclonal antibody or the CDRs. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the $V_L$ and $V_H$ regions joined by the flexible linker (see e.g., Bird et al., (1988) *Science* 242:423-426; Huston et al., (1988) *Proc. Natl. Acad. Sci. USA* 85:5879-5883; McCafferty et al., (1990) *Nature* 348:552-554).

Monoclonal antibodies (mAbs) of the present disclosure can be produced using the well-known somatic cell hybridization (hybridoma) technique of Kohler and Milstein (1975) *Nature* 256:495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

Antibodies of the disclosure also can be produced in a host cell transfectoma using, for example, a combination of recombinant DNA techniques and gene transfection methods as is well known in the art (e.g., Morrison. S. (1985) Science 229:1202). In one embodiment. DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185. Academic Press. San Diego, Calif. (1990)). Preferred regulatory sequences for mammalian host cell expression include viral elements that direct high levels of protein expression in mammalian cells, such as promoters and/or enhancers derived from cytomegalovirus (CMV). Simian Virus 40 (SV40), adenovirus, e.g., the adenovirus major late promoter (AdMLP) and polyomavirus enhancer. Alternatively, non-viral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., (1988) Mol. Cell. Biol. 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation. DEAE-dextran transfection and the like. Although it is theoretically possible to express the antibodies of the disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the disclosure include Chinese Hamster Ovary (CHO cells) (including dhfr-CHO cells, described in Urlaub and Chasin. (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621). NSO myeloma cells. COS cells and SP2 cells. In particular for use with NSO myeloma cells, another preferred expression system is the GS gene expression system disclosed in WO 87/04462. WO 89/01036 and EP 338.841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

In another aspect, the present disclosure features bispecific molecules which may comprise one or more antibodies of the disclosure linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities.

In an embodiment, a bispecific molecule has, in addition to an anti-Fc binding specificity and an anti-C5 binding specificity, a third specificity. The third specificity may be for another complement protein, such as C3, to better inhibit complement mediated inflammation and/or hemolysis.

Bispecific molecules may be in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs (scFv) 2 construct. Intermediate-sized bispecific molecules include two different F (ab) fragments linked by a peptidyl linker. Bispecific molecules of these and other formats can be prepared by genetic engineering, somatic hybridization, or chemical methods. See, e.g., Kufer et al, cited supra; Cao and Suresh, *Bioconjugate Chemistry,* 9 (6). 635-644 (1998); and van Spriel et al., *Immunology Today.* 21 (8). 391-397 (2000), and the references cited therein.

Antibodies of the disclosure can be conjugated to a therapeutic agent to form an immunoconjugate such as an antibody-drug conjugate (ADC). Suitable therapeutic agents include an anti-inflammatory agent. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038,658; WO 07/051,081; WO 07/059.404; WO 08/083,312; and WO 08/103,693; U.S. Patent Publications 20060024317; 20060004081; and 20060247295; the disclosures of which are incorporated herein by reference.

Also provided herein are a chimeric antigen receptor (CAR) containing an anti-C5 scFv, the anti-C5 scFv may comprise CDRs and heavy/light chain variable regions described herein.

The anti-C5 CAR may comprise (a) an extracellular antigen binding domain which may comprise an anti-C5 scFv; (b) a transmembrane domain; and (c) an intracellular signaling domain.

The CAR may contain a signal peptide at the N-terminus of the extracellular antigen binding domain that directs the nascent receptor into the endoplasmic reticulum, and a hinge peptide at the N-terminus of the extracellular antigen binding domain that makes the receptor more available for binding. The CAR preferably comprises, at the intracellular signaling domain, a primary intracellular signaling domain and one or more co-stimulatory signaling domains. The mainly used and most effective primary intracellular signaling domain is CD3-zeta cytoplasmic domain which contains ITAMs, the phosphorylation of which results in T cell activation. The co-stimulatory signaling domain may be derived from the co-stimulatory proteins such as CD28, CD137 and OX40.

The CARs may further add factors that enhance T cell expansion, persistence, and anti-tumor activity, such as cytokines, and co-stimulatory ligands.

Also provided are engineered immune effector cells, which may comprise the CAR provided herein. In some embodiments, the immune effector cell is a T cell, an NK cell, a peripheral blood mononuclear cell (PBMC), a hematopoietic stem cell, a pluripotent stem cell, or an embryonic stem cell. In some embodiments, the immune effector cell is a T cell.

In another aspect, the present disclosure provides a pharmaceutical composition which may comprise one or more antibodies (or antigen-binding portion thereof, or the bispecifics, CAR-T cells, oncolytic viruses, immunoconjugates) of the present disclosure formulated together with a pharmaceutically acceptable carrier. The antibodies (or antigen-binding portion thereof, or the bispecifics, CAR-T cells, oncolytic viruses, immunoconjugates) can be dosed separately when the composition contains more than one antibody (or antigen-binding portion thereof, or the bispecifics, CAR-T cells, oncolytic viruses, immunoconjugates). The composition may optionally contain one or more additional pharmaceutically active ingredients, such as another antibody or a drug, such as an inflammatory agent.

The pharmaceutical composition may comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients are taught in Gennaro, ed., Remington: *The Science and Practice of Pharmacy.* 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion. Alternatively, an antibody or an antigen-binding portion thereof of the disclosure can be administered via a non-parenteral route, such as a topical, epidermal or mucosal route of administration. e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about ninety-nine percent of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for case of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

For administration of the composition, the dosage may range from about 0.0001 to 100 mg/kg, and more usually 0.01 to 5 mg/kg, of the host body weight. For example, dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-C5 antibody of the disclosure include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 μg/ml and in some methods about 25-300 μg/ml.

A "therapeutically effective dosage" of an anti-C5 antibody, or the antigen-binding portion thereof, or the bispecifics, CAR-T cells, oncolytic viruses, immunoconjugates of the disclosure preferably results in a decrease in severity of disease symptoms, an increase in frequency and duration of disease symptom-free periods, or a prevention of impairment or disability due to the disease affliction.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker. Inc., New York. 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the monoclonal antibody or antigen-binding portion thereof of the disclosure can be formulated to ensure proper distribution in vivo. For example, to ensure that the therapeutic antibody or antigen-binding portion thereof of the disclosure cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al., (1995) *FEBS Lett.* 357:140; M. Owais et al., (1995) *Antimicrob. Agents Chemother.* 39: 180; Briscoe et al., (1995) *Am. J. Physiol.* 1233: 134; Schreier et al., (1994) *J. Biol. Chem.* 269:9090; Keinanen and Laukkanen (1994) *FEBS Lett.* 346:123; and Killion and Fidler (1994) *Immunomethods* 4:273.

The pharmaceutical composition which may comprise the antibodies or the antigen-binding portion thereof, or the bispecifics, CAR-T cells, oncolytic viruses, immunoconjugates of the present disclosure have numerous in vitro and in vivo utilities involving, for example, treatment of inflammatory or hemolytic diseases with excessive C5a and/or C5b production.

Given the ability of anti-C5 antibodies of the disclosure to inhibit C5 cleavage into C5a and C5b, the disclosure provides methods for treatment of a complement-mediated inflammatory disease such as an autoimmune disease, which may comprise administering to the subject the pharmaceutical composition of the disclosure. The inflammatory disease includes, but not limited to, gMG and NMOSD.

In another respect, given of anti-C5 antibodies of the disclosure to block C5 cleavage into C5a and C5b, the disclosure provides methods for treating a complement-mediated hemolytic disorder, which may comprise administering to the subject the pharmaceutical composition of the disclosure. The hemolytic disorder includes, but not limited to, PNH and aHUS.

In one aspect, the disclosure provides combination therapy in which the pharmaceutical composition of the present disclosure is co-administered with one or more additional agents that are effective in ameliorating inflammations. Such agents may be prednisone for gMG patients, or azathioprine for NMOSD patients. In certain embodiments, the subject is human.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

Although the present invention and its advantages have been described in detail, it should be understood that various changes, substitutions and alterations can be made herein without departing from the spirit and scope of the invention as defined in the appended claims.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1 Generation of Human Anti-C5 Monoclonal Antibodies Using Hybridoma Technology Immunization A transgenic mouse platform CAMouse$^{HG}$ (HG5042, Chongqing Camab Biotech Ltd.) was used to produce fully human antibodies. The transgenic mice were immunized according to the method as described in E Harlow, D. Lane, Antibody: A Laboratory Manual, Cold Spring Harbor Laboratory Press, Cold Spring Harbor, N.Y., 1998. Recombinant human C5 proteins (Sino biological Inc., Cat #13416-H18H) were used as the immunogen, and also for determining anti-sera titers and screening hybridomas secreting antigen-specific antibodies. Immunizing dosages contained 50 μg human C5 proteins per mouse per injection for primary immunization, and 25 μg human C5 proteins per mouse per injection for boost immunizations. To increase immune response, the complete Freud's adjuvant and incomplete Freud's adjuvant (Sigma, St. Louis. Mo., USA) were used respectively for primary and boost immunizations. Briefly, adjuvant-antigen mixture was prepared as follows. First, the adjuvant was gently mixed in a vial using a vortex. The desired amount of adjuvant was transferred to an autoclaved 1.5 mL micro-centrifuge tube. The antigen was prepared in PBS or saline with concentration ranging from 0.25-0.5 mg/ml. The calculated amount of antigen was then added to the micro-centrifuge tube with the adjuvant, and the resulting mixture was mixed by gently vortexing for 2 minutes to generate water-in-oil emulsions. The adjuvant-antigen emulsion was then drawn into the proper syringe for animal injection. A total of 50 or 25 μg antigen was injected in a volume of 150-200 μl. Each animal was immunized, and then boosted for 3 to 4 times depending on the anti-sera titer. Animals with good titers were given a final boost by intraperitoneal injection before hybridoma fusion.

Hybridoma Fusion and Screening

Cells of murine myeloma cell line (SP2/0-Ag14, ATCC #CRL-1581) were cultured to reach the log phase stage right before fusion. Spleen cells from immunized mice were prepared sterilely and fused with murine myeloma cells according to the method as described in Kohler G, and Milstein C, "Continuous cultures of fused cells secreting antibody of predefined specificity," Nature, 256:495-497 (1975). Fused "hybrid cells" were subsequently dispensed into 96-well plates in DMEM/20% FCS/HAT medium. Surviving hybridoma colonies were observed under the microscope seven to ten days post fusion. After two weeks, the supernatant from each well was subjected to Capture ELISA using human C5 protein (Sino biological Inc., Cat #13416-H18H). Positive hybridomas secreting antibodies that bind to human C5 protein were selected and transferred to 24-well plates. The hybridoma clones were subject to further tests, and those producing antibodies that showed high specific human C5 binding capacities and complement-mediated hemolysis blocking activities were subcloned by limited dilution to ensure the clonality of the cell line. Then, the monoclonal antibodies were purified. Briefly. Protein A sepharose column (from bestchrom (Shanghai) Biosciences, Cat #AA0273) was washed using PBS buffer in 5 to 10 column volumes. The cell supernatant of each monoclonal hybirdoma of the disclosure was passed through the columns, and then the columns were washed using PBS buffer until the absorbance for protein reached the baseline. The columns were eluted with elution buffer (0.1 M Glycine-HCl, pH 2.7), and immediately collected into 1.5 ml tubes with neutralizing buffer (1 M Tris-HCl, pH 9.0). Fractions containing immunoglobulins were pooled and dialyzed in PBS overnight at 4° C.

Subsequently, the in vitro functional activities of purified monoclonal antibodies were characterized as follows.

Example 2 Binding Affinity Determination of Anti-C5 Monoclonal Antibodies Using BIACORE Surface Plasmon Resonance The purified anti-C5 monoclonal antibodies (mAbs) generated in Example 1 were characterized for binding affinities and binding kinetics by Biacore T200 system (GE healthcare, Pittsburgh, PA, USA).

Briefly, goat anti-human IgG (GE healthcare, Cat #BR100839, Human Antibody Capture Kit) was covalently linked to a CM5 chip (carboxy methyl dextran coated chip, GE healthcare, Cat #BR-1005-30) via primary amines, using a standard amine coupling kit provided by Biacore (GE healthcare, Pittsburgh, PA, USA). Un-reacted moieties on the biosensor surface were blocked with ethanolamine. Then, the purified anti-C5 antibodies of the disclosure at the concentration of 13.3 nM and anti-C5 benchmark antibodies (Eculizumab, in house made with the heavy chain and light chain amino acid sequences set forth in SEQ ID NOs: 51 and 52; Crovalimab, in house made with the heavy chain and light chain amino acid sequences set forth in SEQ ID NOs: 55 and 56; Pozelimab, in house made with the heavy chain and light chain amino acid sequences of SEQ ID NOs: 57 and 58) at 13.3 nM, were respectively flowed onto the chip at a flow rate of 10 μL/min. The sequence information of the three anti-C5 benchmark antibodies was from the public website (https://tabs.craic.com). Then, serially diluted recombinant human C5-his proteins (Sino Biological Inc., Cat #13416-H18H), cynomolgus monkey C5-his proteins (Acro biosystems, Cat #CO5-C52Hx), or mutant human C5 (R885H)-his proteins (Acro biosystems, Cat #CO5-H52Hx) (80.0 nM-2.5 nM, 2-fold serial dilution in HBS-EP$^+$ buffer) were flown onto the chip at a flow rate of 30 μL/min. The antigen-antibody association kinetics was followed for 2 minutes and the dissociation kinetics was followed for 10 minutes. The association and dissociation curves were fit to a 1:1 Langmuir binding model using BIAcore evaluation software. The $K_D$, $K_a$ and $K_d$ values were determined and summarized in Tables 2-1 and 2-2 below.

All the anti-C5 antibodies of the disclosure specifically bound to wild type and mutant human C5 proteins with comparable or a bit higher binding affinities than the benchmark antibodies, with A3C8E4H1 and A5H1D11A7 showing the highest binding affinities. All the anti-C5 antibodies of the disclosure specifically bound to monkey C5, while the benchmark Eculizumab did not.

TABLE 2-1

Binding affinity of anti-C5 antibodies to Human C5 and Cynomolgus C5

| | Human C5-his | | | Cynomolgus C5-his | | |
|---|---|---|---|---|---|---|
| mAb ID# | $K_a$ ($M^{-1}s^{-1}$) | $K_d$ ($s^{-1}$) | $K_D$ (M) | $K_a$ ($M^{-1}s^{-1}$) | $K_d$ ($s^{-1}$) | $K_D$ (M) |
| A3C8E4H1 | 1.50E+05 | 1.92E−05 | 1.28E−10 | 2.90E+05 | 4.56E−05 | 1.57E−10 |
| A5H1D11A7 | 1.66E+05 | 3.09E−05 | 1.86E−10 | 3.46E+05 | 5.89E−05 | 1.70E−10 |
| A5G9C2C7 | 1.33E+05 | 3.47E−05 | 2.62E−10 | 1.85E+05 | 2.93E−04 | 1.58E−09 |
| A5G2A1A1 | 6.90E+04 | 2.85E−05 | 4.13E−10 | 1.65E+05 | 4.44E−03 | 2.70E−08 |
| A3B4H8H7 | 1.47E+05 | 7.67E−05 | 5.23E−10 | 3.77E+05 | 4.19E−04 | 1.11E−09 |
| A6A1H9B7 | 1.12E+05 | 7.26E−05 | 6.47E−10 | 2.94E+05 | 4.21E−04 | 1.43E−09 |
| A5F3D5A1 | 1.04E+05 | 8.83E−05 | 8.54E−10 | 2.60E+05 | 4.14E−04 | 1.59E−09 |
| A4G10B7A7 | 1.04E+05 | 9.50E−05 | 9.12E−10 | 2.62E+05 | 3.87E−04 | 1.47E−09 |
| A2E12G12H7 | 1.17E+05 | 1.86E−04 | 1.60E−09 | 3.60E+05 | 2.67E−04 | 7.41E−10 |
| Eculizumab | 6.12E+04 | 4.23E−05 | 6.91E−10 | | No-binding | |

TABLE 2-2

Binding affinity of anti-C5 antibodies to mutant human C5

| | Human C5 (R885H)-his | | |
|---|---|---|---|
| mAb ID# | $K_a$ ($M^{-1}s^{-1}$) | $K_d$ ($s^{-1}$) | $K_D$ (M) |
| A3C8E4H1 | 3.09E+05 | 1.96E−05 | 6.35E−11 |
| A5H1D11A7 | 3.69E+05 | 2.67E−05 | 7.23E−11 |
| A5G9C2C7 | 5.05E+05 | 1.53E−04 | 3.03E−10 |
| A5G2A1A1 | 3.05E+05 | 3.50E−05 | 1.15E−10 |
| A3B4H8H7 | 4.49E+05 | 2.48E−04 | 5.52E−10 |
| A6A1H9B7 | 2.58E+05 | 2.11E−04 | 8.18E−10 |
| A5F3D5A1 | 2.78E+05 | 2.03E−04 | 7.30E−10 |
| A4G10B7A7 | 3.60E+05 | 2.31E−04 | 6.42E−10 |
| A2E12G12H7 | 3.08E+05 | 4.08E−04 | 1.32E−09 |
| Crovalimab | 3.87E+05 | 1.13E−04 | 2.93E−10 |
| Pozelimab | 1.18E+06 | 1.33E−04 | 1.12E−10 |

Example 3 Binding Activities of Anti-C5 Antibodies

The antibodies of the disclosure were further tested for their binding capacities to C5 by Capture ELISA and indirect ELISA.

3.1 Capture ELISA

Briefly, 96-well plates were coated with 2 μg/ml AffiniPure Goat Anti-Human IgG, Fcγ fragment specific (Jackson Immuno Research, Cat #109-005-098) in PBS, 100 μl/well, for 2 hours at 37° C. Plates were washed once with wash buffer (PBS+0.05% Tween-20, PBST) and then blocked with 200 μl/well blocking buffer (5% w/v non-fatty milk in PBST) overnight at 4° C. Plates were washed again, respectively incubated with 100 μl/well serially diluted anti-C5 antibodies of the disclosure, Eculizumab and hIgG (human immunoglobulin (pH4) for intravenous injection, Hualan Biological Engineering Inc.) (5-fold dilution in 2.5% non-fatty milk in PBST, starting at 66.7 nM) for 40 minutes at 37° C., and washed 4 times again. Plates containing captured antibodies were incubated with 100 μl/well biotin-labeled human C5-his proteins (Sino biological Inc., Cat #13416-H18H, 0.99 nM in 2.5% non-fatty milk in PBST) for 40 minutes at 37° C., washed 4 times, and incubated with streptavidin conjugated HRP (1:5000 dilution in PBST, Jackson Immuno Research, Cat #016-030-084, 100 μl/well) for 40 minutes at 37° C. After a final wash, plates were incubated with 100 μl/well ELISA substrate TMB (Innoreagents, Cat #TMB-S-002). The reaction was stopped 3 minutes later at room temperature with 50 μl/well 1M $H_2SO_4$. Absorbance of each well was read on a microplate reader using dual wavelength mode with 450 nm for TMB and 630 nm as the reference wavelength, and the OD (450-630) values were plotted against antibody concentration. Data was analyzed using Graphpad Prism software and $EC_{50}$ values were reported.

3.2 Indirect ELISA

The anti-C5 antibodies' cross-reactions to cynomolgus or human C5 mutant proteins were measured.

Briefly, 96-well micro plates were coated with 1 μg/ml cynomolgus C5-his proteins (Acro biosystems, Cat #CO5-C52Hx) or 2 μg/ml human C5 (R885H)-his proteins (Acro biosystems, Cat #CO5-H52Hx) in carbonate/bicarbonate buffer (pH 9.6), 100 μl/well, for 2 hours at 37° C. ELISA plates were washed once with wash buffer (PBS+0.05% Tween-20, PBST) and then blocked with 200 μl/well blocking buffer (5% w/v non-fatty milk in PBST) overnight at 4° C. Plates were washed again and incubated with 100 μl/well serially diluted anti-C5 antibodies of the disclosure or controls (66.7-0.64 nM. 5-fold serial dilution in PBST with 2.5% non-fatty milk) for 40 minutes at 37° C. ELISA plates were washed 4 times and incubated with Peroxidase AffiniPure F(ab')$_2$ Fragment Goat Anti-Human IgG. Fcγ fragment specific (1:5000 dilution in PBST buffer. Jackson Immunoresearch. Cat #109-036-098, 100 μl/well) for 40 minutes at 37° C. After a final wash, plates were incubated with 100 μl/well TMB (Innoreagents, Cat #TMB-S-002). The reaction was stopped 3 minutes later at room temperature with 50 μl/well 1M $H_2SO_4$. Absorbance of each well was read on a microplate reader using dual wavelength mode with 450 nm for TMB and 630 nm as the reference wavelength, and the OD (450-630) values were plotted against antibody concentration. Data was analyzed using Graphpad Prism software and $EC_{50}$ values were reported.

The results of the two assays were shown FIGS. 1A-1C to 3A-3C.

Figure 1B:
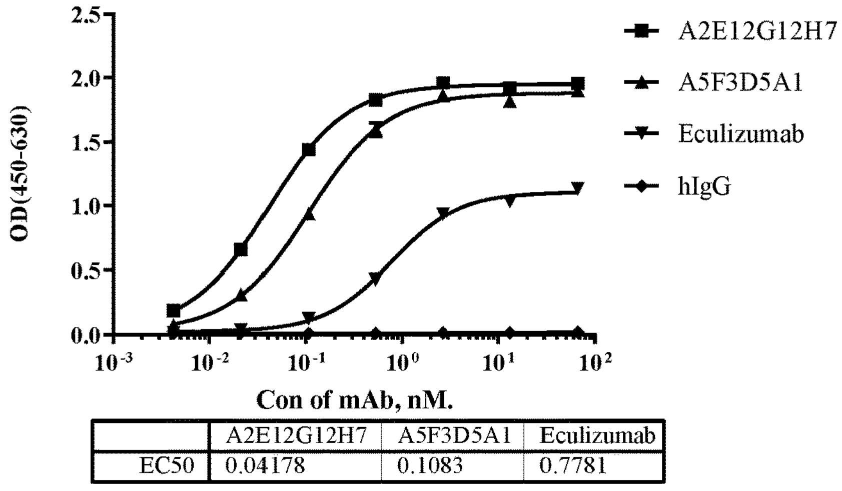
Figure 1C:
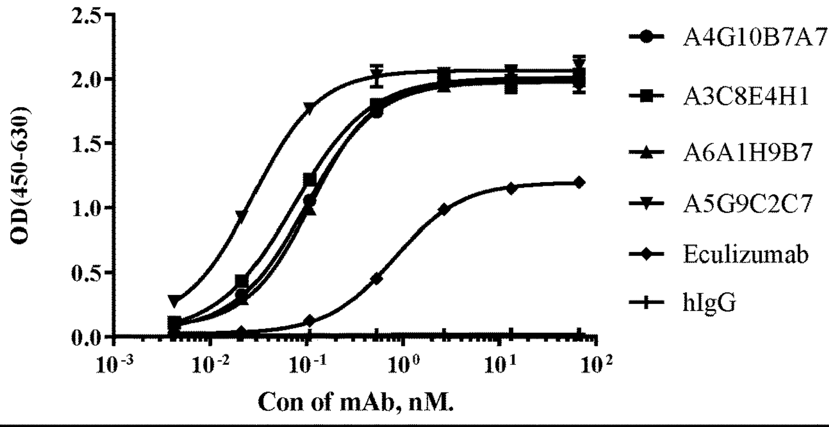

It can be seen from FIGS. 1A-1C that all antibodies of the disclosure bound to human C5 with lower $EC_{50}$ and higher Bmax (maximum binding) than Eculizumab.

Figure 2A:
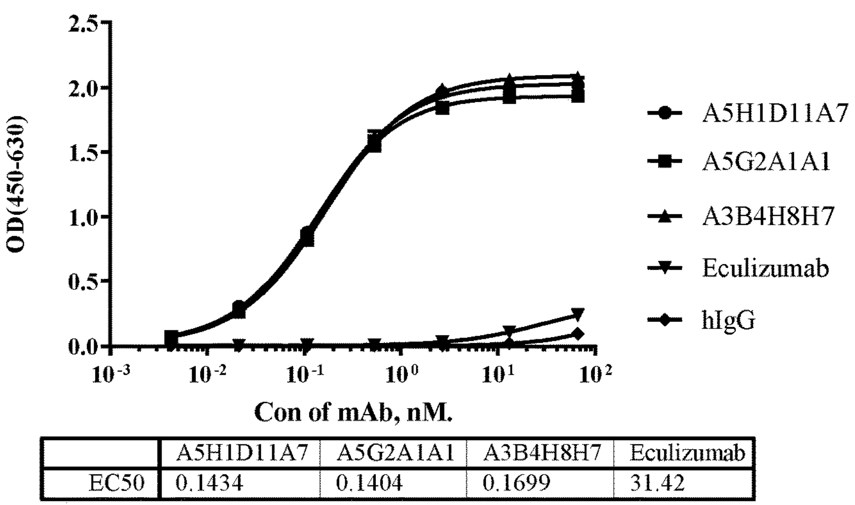
FIGS. 2A-2C show the binding capacities of antibodies A5H1D11A7, A5G2A1A1 and A3B4H8H7 (A), A2E12G12H7 and A5F3D5A1 (B), A4G10B7A7, A3C8E4H1, A6A1H9B7 and A5G9C2C7 (C) to cynomolgus C5 in an indirect ELISA.
Figure 2B:
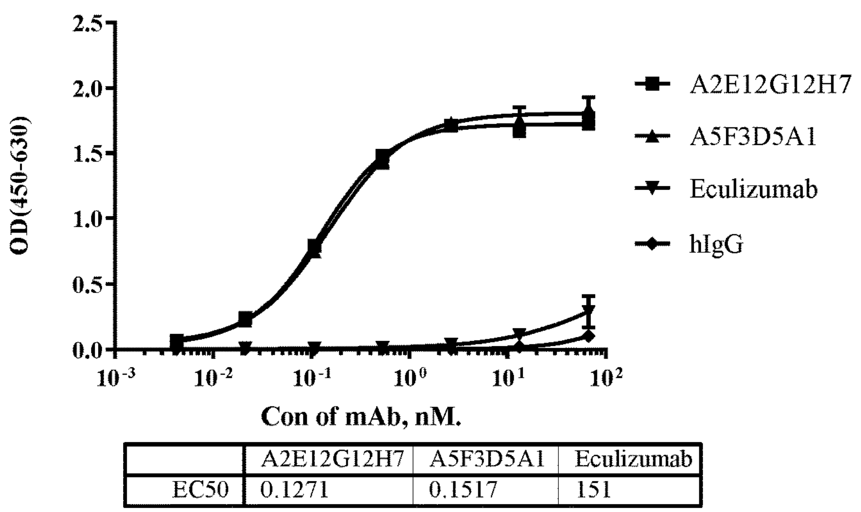
Figure 2C:
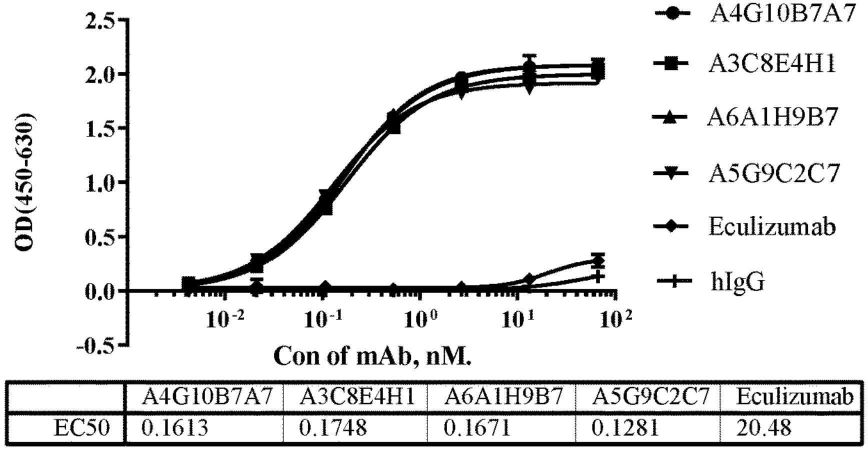

FIGS. 2A-2C showed that all antibodies of the disclosure bound to monkey C5 with low $EC_{50}$ and high Bmax (maximum binding), and Eculizumab did not bind monkey C5 proteins.

Figure 3A:
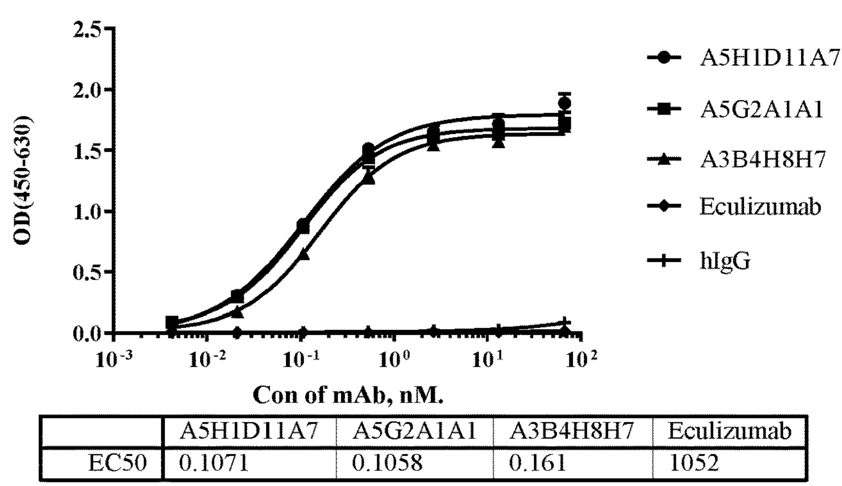
FIGS. 3A-3C shows the binding capacities of antibodies A5H1D11A7, A5G2A1A1 and A3B4H8H7 (A), A2E12G12H7, A5F3D5A1, A4G10B7A7 and A3C8E4H1 (B), A6A1H9B7 and A5G9C2C7 (C) to mutant human C5 in an indirect ELISA.
Figure 3B:
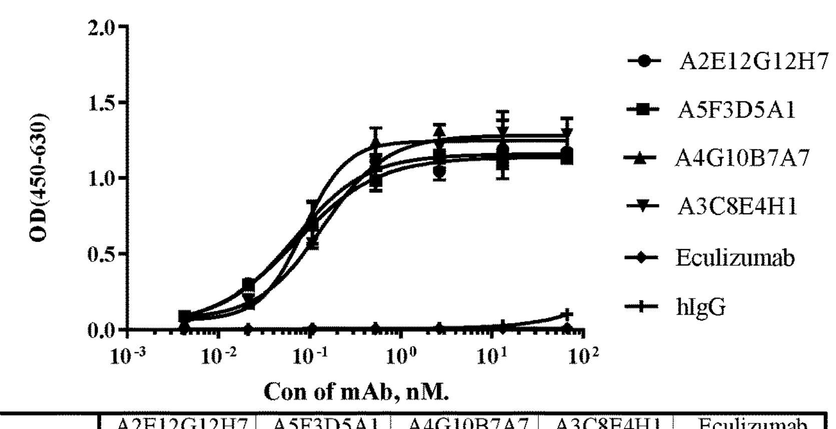
Figure 3C:
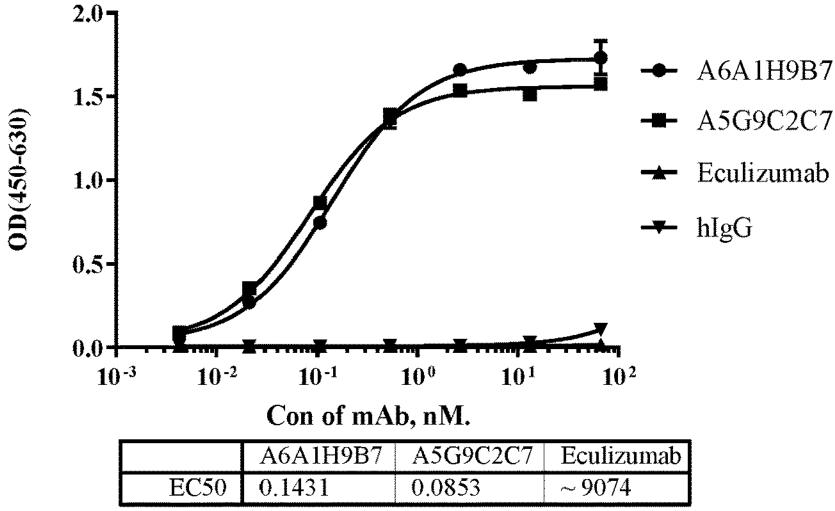

Further, as shown in FIGS. 3A-3C, all antibodies of the disclosure bound to mutant human C5 (R885H) protein with low $EC_{50}$ and high Bmax (maximum binding), while Eculizumab did not bound to the mutant human C5 (R885H) protein.

Example 4 Blocking Activities of Anti-C5 Antibodies on C5-Benchmark Binding

The abilities of the anti-C5 antibodies of the disclosure to block Eculizumab-human C5 binding was measured in a competitive ELISA assay.

Briefly, Eculizumab was coated on 96-well micro plates at 2 μg/mL in PBS. 100 μl per well, for 2 hours at 37° C. Then plates were washed with wash buffer, and blocked with 5% w/v non-fatty milk in PBST overnight at 4° C. The next day, the anti-C5 antibodies of the disclosure or controls were diluted with biotin labeled human C5-his protein (Sino biological Inc., Cat #13416-H18H, 0.99 nM in PBST with 2.5% non-fatty milk), starting at 80 nM with a 4-fold serial dilution, and incubated at room temperature for 40 minutes. After plate washing, the antibody/C5-his mixtures were added to Eculizumab coated plates, 100 μl per well. After incubation at 37° C., for 40 minutes, plates were washed using wash buffer. Then the plates were added and incubated with 100 μl/well streptavidin conjugated HRP for 40 minutes at 37° C., to detect biotin labeled human C5-his bound to Eculizumab. Plates were washed again using wash buffer. Finally. TMB was added and the reaction was stopped using 1M $H_2SO_4$. The absorbance of each well was read on a microplate reader using dual wavelength mode with 450 nm for TMB and 630 nm as the reference wavelength, and the OD (450-630) values were plotted against antibody concentration. Data was analyzed using Graphpad Prism software and $IC_{50}$ values were reported.

The ability of the antibody A5H1D11A7 of the disclosure to block binding of Pozelimab to human C5 protein was also measured in a competitive ELISA assay. Briefly. Pozelimab was coated on 96-well micro plates at 2 μg/mL in carbonate/bicarbonate buffer (pH 9.6), 100 μl/well, and incubated overnight at 4° C. ELISA plates were washed once with wash buffer (PBS+0.05% Tween-20. PBST) and then blocked with 200 μl/well blocking buffer (5% w/v non-fatty milk in PBST) for 2 hours at 37° C. While blocking, the anti-C5 antibody A5H1D11A7 of the disclosure or controls were diluted with human C5 (R885H)-his protein (Acro biosystems, Cat #CO5-H52Hx, 40 ng/ml in 2.5% non-fatty milk in PBST), starting at 66.7 nM with a 4-fold serial dilution, and incubated at room temperature for 40 minutes. After plate washing, the antibody/C5 protein mixtures were added to Pozelimab coated plates, 100 μl per well. After incubation at 37° C., for 40 minutes, plates were washed using wash buffer. Then the plates were added and incubated with 100 μl/well anti-His-Tag antibody conjugated with HRP (Sinobiological, Cat #: 105327-MM02T-H) for 40 minutes at 37° C., to detect human C5 (R885H)-his bound to Pozelimab. Plates were washed again using wash buffer. Finally, TMB was added and the reaction was stopped using 1M $H_2SO_4$. The absorbance of each well was read on a microplate reader using dual wavelength mode with 450 nm for TMB and 630 nm as the reference wavelength, and the OD (450-630) values were plotted against antibody concentration. Data was analyzed using Graphpad Prism software and $IC_{50}$ values were reported.

The results were shown in FIGS. 4A-4C and FIG. 5.

Figure 4A:
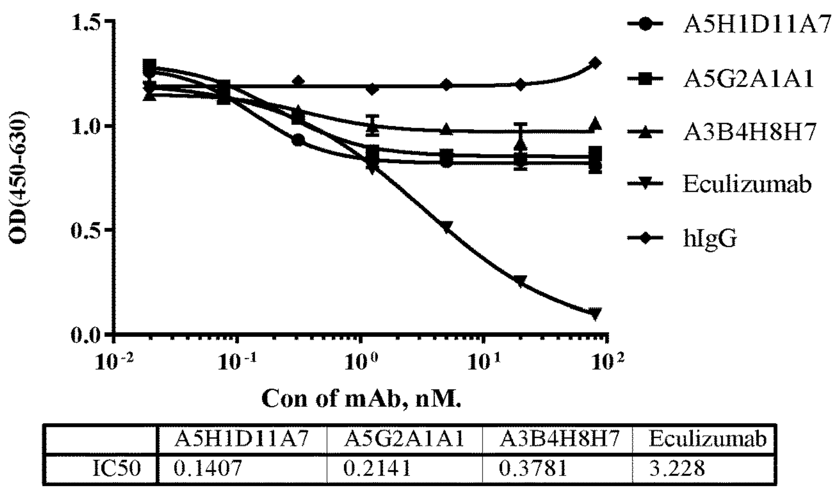
FIGS. 4A-4C show the abilities of antibodies A5H1D11A7. A5G2A1A1 and A3B4H8H7 (A), A2E12G12H7 and A5F3D5A1 (B), A4G10B7A7, A3C8E4H1, A6A1H9B7 and A5G9C2C7 (C) to block eculizumab-human C5 binding in a competitive ELISA.
Figure 4B:
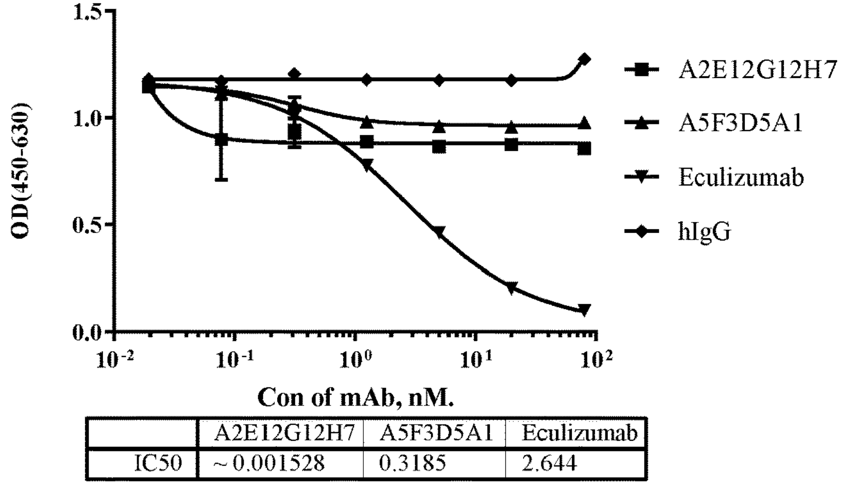
Figure 4C:
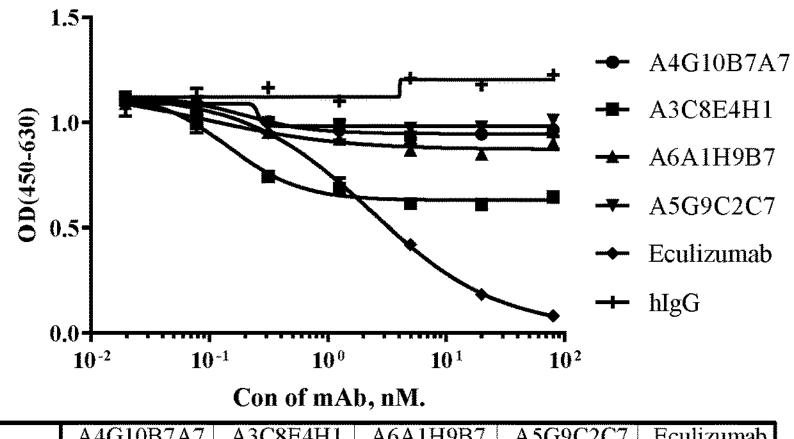

It can be seen from FIGS. 4A-4C that the anti-C5 antibodies of the disclosure were unable to or can only partially block human C5-Eculizumab interaction, suggesting that they might bind to a different epitope as compared to Eculizumab.

Figure 5:
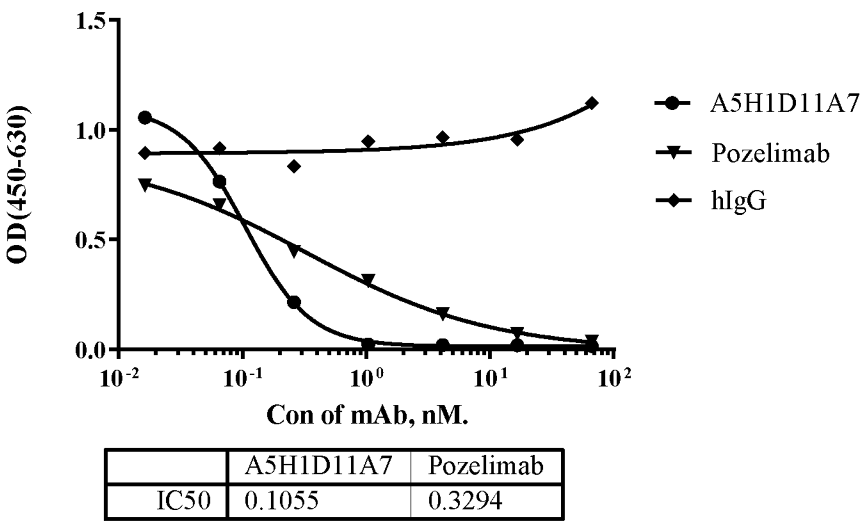
FIG. 5 shows the abilities of antibodies A5H1D11A7 to block pozelimab-human C5 binding in a competitive ELISA.

FIG. 5 showed that the anti-C5 antibody A5H1D11A7 was able to block C5 binding to Pozelimab, suggesting that the A5H1D11A7 antibody might bind to the same or similar epitope as Pozelimab did.

Example 5 Thermal Stabilities of Anti-C5 Antibodies

The anti-C5 antibodies A5H1D11A7 and A3C8E4H1 were tested for the thermal stabilities. Briefly, a protein thermal shift assay was used to determine Tm (melting temperature) using a GloMelt™ Thermal Shift Protein Stability Kit (Biotium, Cat #33022-T). The GloMelt™ dye was allowed to thaw and reach room temperature. The vial containing the dye was vortexed and centrifuged. Then, 10× dye was prepared by adding 5 μL 200× dye to 95 μL PBS. Then, 2 μL 10× dye was added to 10 μg antibodies, and then PBS was added to a total reaction volume of 20 μL. The tubes containing the dye and antibodies were briefly spun and placed in real-time PCR thermocycler (Roche. LightCycler 480 II) set up with a melt curve program having the parameters in Table 3.

TABLE 3

Parameters for Melt Curve Program

| Profile step | Temperature | Ramp rate | Holding Time |
|---|---|---|---|
| Initial hold | 25° C. | NA | 30 s |
| Melt curve | 25-99° C. | 0.1° C./s | NA |

Figure 6A:
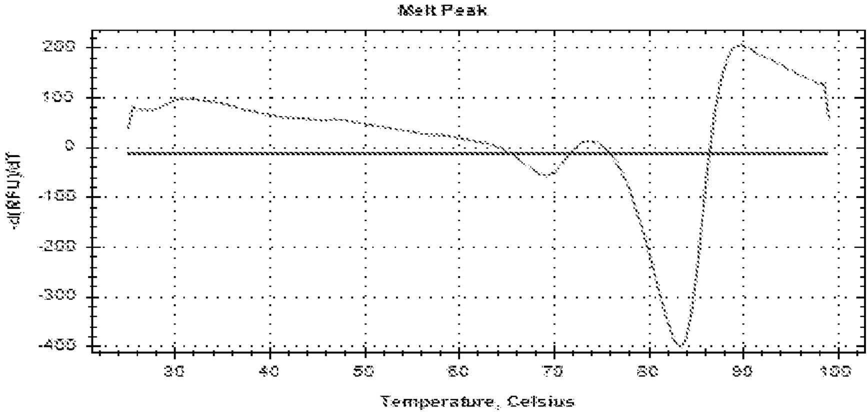
FIGS. 6A-6B show the protein thermal shift assay results of the antibodies A5H1D11A7 (A) and A3C8E4H1 (B).
Figure 6B:
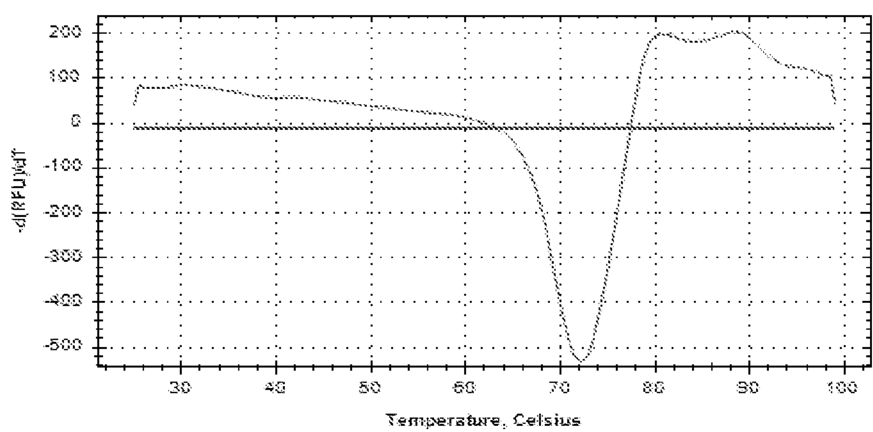

The results were shown in FIGS. 6A-6B and Table 4, suggesting that the two antibodies were probably stable in human body.

TABLE 4

Melting temperatures of anti-C5 antibodies

| | Tm (melting temperature) ° C. | |
|---|---|---|
| mAb ID# | Tm1 | Tm2 |
| A5H1D11A7 | 69 | 83.5 |
| A3C8E4H1 | 72 | NA |
| Crovalimab | 76.5 | NA |
| Pozelimab | 65.5 | NA |

Example 6 Inhibition of Complement-Mediated Hemolysis by Anti-C5 Antibodies

The anti-C5 antibodies of the disclosure were further tested for their inhibitory effects on complement-mediated hemolysis.

Briefly, sheep red blood cells (sRBCs) (Zhengzhou Baiji biological Inc., Cat #C0001) were washed 5 times with gelatin/veronal-buffered saline containing 0.5 nM $MgCl_2$ and 0.15 nM $CaCl_2$ (GVB++) and were re-suspended in the same buffer at $5.87\times10^8$ cells/mL. Then, the cell suspensions were mixed with rabbit anti-sheep RBC immunoglobulins (Zhengzhou Baiji biological Inc., Cat #A0001, 1:1000 dilution in GVB++) at 1:1 volume ratio, and incubated at 37° C., for 30 minutes. Cells were washed twice with GVB++, and re-suspended in the same buffer at $2\times10^8$ cells/mL. In a separate round-bottom 96-well micro plate, 50 μL of 3% normal human serum (Gemini biological Inc., Cat #100-512) in GVB++ was added with 50 μL of serially diluted anti-C5 antibodies of the disclosure or controls (including an in house made anti-CD22 antibody as negative control) (starting at 1200 nM with a 3-fold serial dilution in GVB++) and incubated at room temperature for 30 minutes. Then, 50 μL of the suspension with sensitized sRBCs was added to the serum/antibody, a total of 150 μL in each well (the final ratio for normal human serum was 1%), and the resultant mixture was incubated at 37° C., for 1 hour. After the incubation, the plate was centrifuged at 3000 rpm for 5 minutes at 4° C. Supernatants were transferred to wells on a flat-bottom 96-well micro plate for OD measurement at 412 nm. The percent hemolysis was defined as $100\times[(OD_{antibody}-OD_{background})/(OD_{no\text{-}antibody}-OD_{background})]$. Data was analyzed using Graphpad Prism software and $IC_{50}$ values were reported.

Figure 7A:
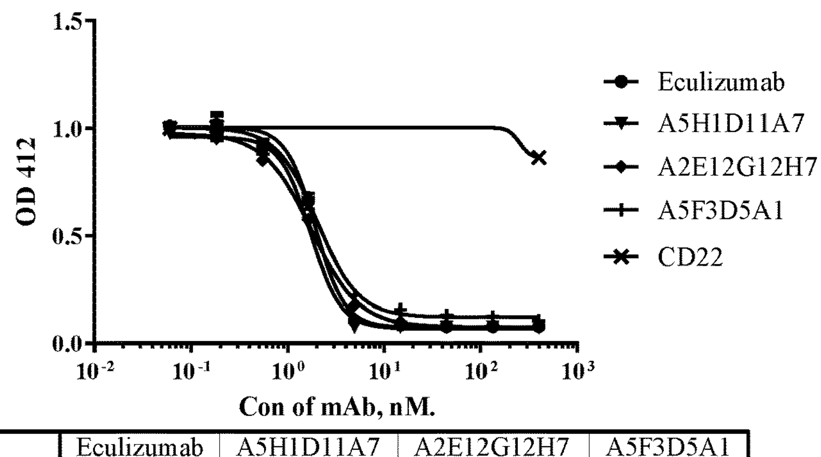
FIGS. 7A-7C show the effects of antibodies A5H1D11A7. A2E12G12H7 and A5F3D5A1 (A), A4G10B7A7, A3C8E4H1 and A6A1H9B7 (B), A5G2A1A1, A3B4H8H7 and A5G9C2C7 (C) on complement-mediated hemolysis in a cell based functional assay.
Figure 7B:
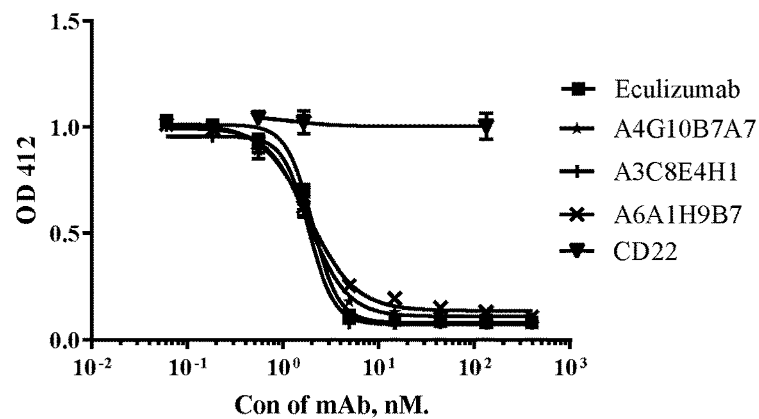
Figure 7C:
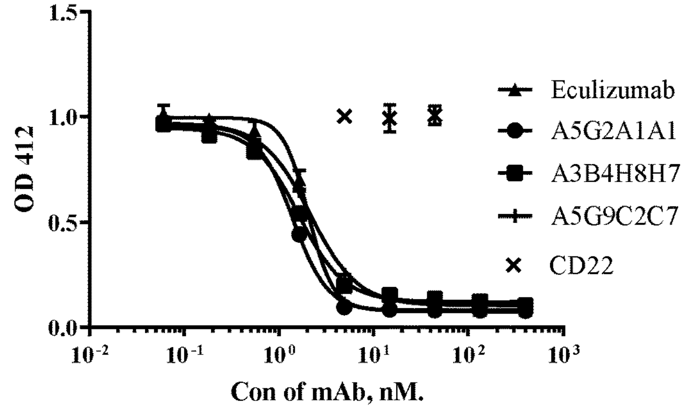

The results were shown in FIGS. 7A to 7C.

It can be seen that the anti-C5 antibodies of the disclosure were able to inhibit the complement-mediated hemolysis, at comparable or a bit higher inhibitory activities as compared to Eculizumab.

The anti-C5 antibody A5H1D11A7 was tested again for its inhibitory effect on complement-mediated hemolysis compared with prior art anti-C5 antibodies, including eculizumab, ravulizumab (in house made with the heavy chain and light chain amino acid sequences set forth in SEQ ID NOs: 53 and 54), crovalimab and pozelimab, following the protocol above with minor modifications.

Briefly, 100% normal human serum (Gemini biological inc., Cat #100-512) was used instead of 3% normal human serum, 50 μl/well; and the anti-C5 antibodies of the disclosure and controls were prepared with a 2-fold serial dilution in GVB++, with a starting concentration at 1800 nM. The results were shown in FIG. 8.

Figure 8:
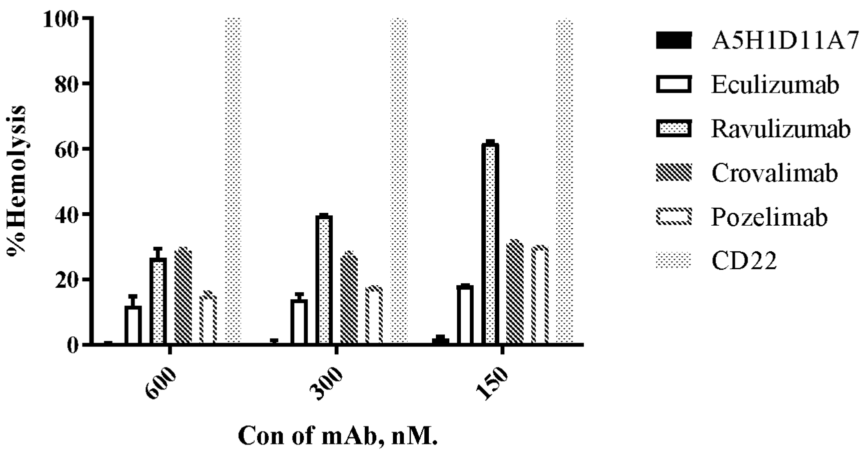
FIG. 8 shows the percent hemolysis in the sample treated by antibody A5H1D11A7 in a complement-mediated hemolysis assay.

According to the FIG. 8, the anti-C5 antibody A5H1D11A7 showed significantly higher inhibitory effects on complement-mediated hemolysis than all the prior art anti-C5 antibodies.

The anti-C5 antibodies A5H1D11A7 and A3C8E4H1 were tested again for their inhibitory effects on complement-mediated hemolysis compared with prior art anti-C5 antibody Eculizumab, following the protocol above with minor modifications. In specific, 50% normal human serum (Gemini biological inc., Cat #100-512) was used instead of 3% normal human serum, 50 μl/well; and the anti-C5 antibodies of the disclosure and controls were prepared with a 2-fold serial dilution in GVB++, with a starting concentration at 600 nM. The results were shown in FIG. 9.

Figure 9:
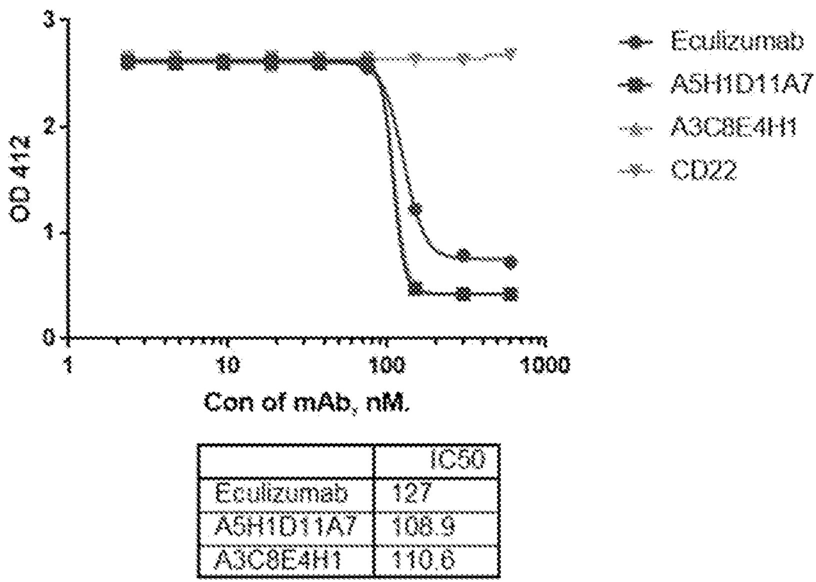
FIG. 9 shows the effects of antibodies A5H1D11A7 and A3C8E4H1 on complement-mediated hemolysis in a cell based functional assay.

According to the FIG. 9, the curves of A5H1D11A7 and A3C8E4H1 almost completely overlapped, with close $IC_{50}$ values. Further, A5H1D11A7 and A3C8E4H1 showed higher capacities of blocking complement-mediated hemolysis than Eculizumab.

Example 7 Sequencing of Anti-C5 Antibodies

All anti-C5 antibodies of the disclosure were sequenced, and complete heavy chain and light chain variable region sequences and constant region sequences were obtained.

The sequence ID NOs of the heavy chain and light chain variable regions were listed in Table 1, and the isotypes of the heavy and light chains were determined to be human IgG1 and kappa respectively by sequence alignment in database.

While the disclosure has been described above in connection with one or more embodiments, it should be understood that the disclosure is not limited to those embodiments, and the description is intended to cover all alternatives, modifications, and equivalents, as may be included within the spirit and scope of the appended claims. All referenced cited herein are further incorporated by reference in their entirety.

Sequences in the present application are summarized below.

| Description/ Sequence/SEQ ID NO. |
|---|
| VH CDR1 for A5H1D11A7<br>SGSYYWS (SEQ ID NO: 1) |
| VH CDR2 for A5H1D11A7<br>HIYYSGSTYFNPSLKS (SEQ ID NO: 7) |
| VH CDR3 for A5H1D11A7<br>GYGGYGYLDN (SEQ ID NO: 14) |
| VL CDR1 for A5H1D11A7<br>RASQGIRDDLG (SEQ ID NO: 20) |
| VL CDR2 for A5H1D11A7<br>AASTLQS (SEQ ID NO: 25) |
| VL CDR3 for A5H1D11A7<br>LQDSNYPWT (SEQ ID NO: 31) |
| VH for A5H1D11A7<br>QVQLQESGPGLVKPSQTLSLTCTVSGGSLSSGSYYWSWIRQHPGKGLEWIGHIYYSGSTYF<br>NPSLKSRLTMSVDTSKNQFSLRLSSVTAADTAVYYCARGYGGYGYLDNWGQGTLVTVSS<br>(SEQ ID NO: 38) |
| VL for A5H1D11A7<br>AIQMTQSPSSLSASVGDX1VTITCRASQGIRDDLGWYQQKPGKAPKLLIFAASTLQSGVPSR<br>FSGSGSGTDFTLTISSLQPEDFATYYCLQDX2NYPWTFGQGTKVEX3K<br>(SEQ ID NO: 44,<br>X1 = S, X2 = S, X3 = F)<br>AIQMTQSPSSLSASVGDSVTITCRASQGIRDDLGWYQQKPGKAPKLLIFAASTLQSGVPSRF<br>SGSGSGTDFTLTISSLQPEDFATYYCLQDSNYPWTFGQGTKVEFK |
| VH CDR1 for A5G2A1A1<br>SGSFYWS (SEQ ID NO: 2) |
| VH CDR2 for A5G2A1A1<br>YIYYSGSTYYNPSLKS (SEQ ID NO: 8) |
| VH CDR3 for A5G2A1A1<br>GYSGYGYFDY (SEQ ID NO: 15) |
| VL CDR1 for A5G2A1A1<br>RASQGIRDDLG (SEQ ID NO: 20) |
| VL CDR2 for A5G2A1A1<br>AASSLQS (SEQ ID NO: 26) |
| VL CDR3 for A5G2A1A1<br>LQDNNFPWT (SEQ ID NO: 32) |
| VH for A5G2A1A1<br>QVQLQESGPGLVKPSQTLSLTCTVSGGSX1SSGSFYWSWIRQLPGKGLEWIGYIYYSGSTY<br>YNPSLKSRLTX2SVDPSKNQFSLKLSSVTAADTAVYYCARGYX3GYGYX4DYWGQGTLVT<br>VSS (SEQ ID NO: 39, X1 = I, X2 = I, X3 = S, X4 = F)<br>QVQLQESGPGLVKPSQTLSLTCTVSGGSISSGSFYWSWIRQLPGKGLEWIGYIYYSGSTYYN<br>PSLKSRLTISVDPSKNQFSLKLSSVTAADTAVYYCARGYSGYGYFDYWGQGTLVTVSS |
| VL for A5G2A1A1<br>AIQMTQSPSSLSASVGDRVTITCRASQGIRDDLGWYQQKPGKAPKLLIYAASSLQSGVPSRF<br>SGSGSGTDFTLTISSLQPEDFATYYCLQDNNFPWTFGQGTKVDFK (SEQ ID NO:59) |
| VH CDR1 for A3C8E4H1<br>SGSFYWS (SEQ ID NO: 2) |
| VH CDR2 for A3C8E4H1<br>YIYYSGSTYYNPSLKS (SEQ ID NO: 8) |
| VH CDR3 for A3C8E4H1<br>GYGGYGYLDY (SEQ ID NO: 16) |

-continued

| Description/ Sequence/SEQ ID NO. |
|---|
| VL CDR1 for A3C8E4H1<br>RASQGIRDDLG (SEQ ID NO: 20) |
| VL CDR2 for A3C8E4H1<br>AASTLQS (SEQ ID NO: 25) |
| VL CDR3 for A3C8E4H1<br>LQDHNYPWT (SEQ ID NO: 33) |
| VH for A3C8E4H1<br>QVQLQESGPGLVKPSQTLSLTCTVSGGSX1SSGSFYWSWIRQLPGKGLEWIGYIYYSGSTY YNPSLKSRLTX2SVDPSKNQFSLKLSSVTAADTAVYYCARGYX3GYGYX4DYWGQGTLVT VSS (SEQ ID NO: 39, X1 = L, X2 = M, X3 = G, X4 = L)<br>QVQLQESGPGLVKPSQTLSLTCTVSGGSLSSGSFYWSWIRQLPGKGLEWIGYIYYSGSTYY NPSLKSRLTMSVDPSKNQFSLKLSSVTAADTAVYYCARGYGGYGYLDYWGQGTLVTVSS |
| VL for A3C8E4H1<br>AIQMTQSPSSLSASVGDX1VTITCRASQGIRDDLGWYQQKPGKAPKLLIFAASTLQSGVPSR FSGSGSGTDFTLTISSLQPEDFATYYCLQDX2NYPWTFGQGTKVEX3K (SEQ ID NO: 44, X1 = T, X2 = H, X3 = I)<br>AIQMTQSPSSLSASVGDTVTITCRASQGIRDDLGWYQQKPGKAPKLLIFAASTLQSGVPSRF SGSGSGTDFTLTISSLQPEDFATYYCLQDHNYPWTFGQGTKVEIK |
| VH CDR1 for A2E12G12H7<br>GYYIH (SEQ ID NO: 3) |
| VH CDR2 for A2E12G12H7<br>WINPNSGSTNSAQKFQD (SEQ ID NO: 9) |
| VH CDR3 for A2E12G12H7<br>RADYYGSGNFYYFDY (SEQ ID NO: 17) |
| VL CDR1 for A2E12G12H7<br>RASQSISRWLA (SEQ ID NO: 21) |
| VL CDR2 for A2E12G12H7<br>AATSLQS (SEQ ID NO: 27) |
| VL CDR3 for A2E12G12H7<br>QQANTEPLI (SEQ ID NO: 34) |
| VH for A2E12G12H7<br>QVQLVQSGAEVKKPGASVKVSCKASGYTFTGYYIHWVRQAPGQGLEWMGWINPNSGST NSAQKFQDWVTLTRDTSISTAYMELSRLKSDDTAVYYCARRADYYGSGNFYYFDYWGQ GTLVTVSS (SEQ ID NO: 40) |
| VL for A2E12G12H7<br>DIQMTQSPSSVSASVGDRVTISCRASQSISRWLAWYQQKPGKAPKLLIYAATSLQSGVPSRF SGSGFVRDFTLTISSLQPEDFATYYCQQANTEPLIFGGGTKVEIK (SEQ ID NO: 45) |
| VH CDR1 for A3B4H8H7<br>SYWIS (SEQ ID NO: 4) |
| VH CDR2 for A3B4H8H7<br>RIDPGDSYTNNSPSFQG (SEQ ID NO: 10) |
| VH CDR3 for A3B4H8H7<br>HHPILATISPDAFDI (SEQ ID NO: 18) |
| VL CDR1 for A3B4H8H7<br>RASQSFSSRYLA (SEQ ID NO: 22) |
| VL CDR2 for A3B4H8H7<br>GAISRAT (SEQ ID NO: 28) |
| VL CDR3 for A3B4H8H7<br>QYYGISPYT (SEQ ID NO: 35) |
| VH for A3B4H8H7<br>EVQLVQSGAEVKKPGESLRISCKGSGYSFTSYWISWVRQMPGKGLEWMGRIDPGDSYX1N X2SPSFQGHVTISADKSISTAYLQWSSLKASDTAMYYCARHHPILATISPDAFDIWGQGTM VTVSS (SEQ ID NO: 41, X1 = T, X2 = N)<br>EVQLVQSGAEVKKPGESLRISCKGSGYSFTSYWISWVRQMPGKGLEWMGRIDPGDSYTNN SPSFQGHVTISADKSISTAYLQWSSLKASDTAMYYCARHHPILATISPDAFDIWGQGTMVT VSS |

-continued

| Description/ Sequence/SEQ ID NO. |
| --- |
| VL for A3B4H8H7<br>EIVLTQSPGTLALSPGERATLSCRASQSFSSRYLAWHQQKPGQAPRLLIFGAISRATGIPDRF SGSGSGTDFTLTISRLEPEDFAVYHCQYYGISPYTFGQGTKLEIK (SEQ ID NO: 46) |
| VH CDR1 for A6A1H9B7<br>SYWIS (SEQ ID NO: 4) |
| VH CDR2 for A6A1H9B7<br>RIDPGDSYSNFSPSFQG (SEQ ID NO: 11) |
| VH CDR3 for A6A 1H9B7<br>HHPILATISPDAFDI (SEQ ID NO: 18) |
| VL CDR1 for A6A1H9B7<br>RASQSFSSRYLA (SEQ ID NO: 22) |
| VL CDR2 for A6A1H9B7<br>GAISRAT (SEQ ID NO: 28) |
| VL CDR3 for A6A1H9B7<br>QYYGISPYT (SEQ ID NO: 35) |
| VH for A6A1H9B7<br>EVQLVQSGAEVKKPGESLRISCKGSGYSFTSYWISWVRQMPGKGLEWMGRIDPGDSYX1N X2SPSFQGHVTISADKSISTAYLQWSSLKASDTAMYYCARHHPILATISPDAFDIWGQGTM VTVSS (SEQ ID NO: 41, X1 = S, X2 = F)<br>EVQLVQSGAEVKKPGESLRISCKGSGYSFTSYWISWVRQMPGKGLEWMGRIDPGDSYSNF SPSFQGHVTISADKSISTAYLQWSSLKASDTAMYYCARHHPILATISPDAFDIWGQGTMVT VSS |
| VL for A6A1H9B7<br>EIVLTQSPGTLALSPGERATLSCRASQSFSSRYLAWHQQKPGQAPRLLIFGAISRATGIPDRF SGSGSGTDFTLTISRLEPEDFAVYHCQYYGISPYTFGQGTKLEIK (SEQ ID NO: 46) |
| VH CDR1 for A4G10B7A7<br>SYWIS (SEQ ID NO: 4) |
| VH CDR2 for A4G10B7A7<br>RIDPSDSYTNNSPSFQG (SEQ ID NO: 12) |
| VH CDR3 for A4G10B7A7<br>HHPILATISPDAFDI (SEQ ID NO: 18) |
| VL CDR1 for A4G10B7A7<br>RASQSISSRYLA (SEQ ID NO: 23) |
| VL CDR2 for A4G10B7A7<br>ATIRRAT (SEQ ID NO: 29) |
| VL CDR3 for A4G10B7A7<br>QKYSISPYT (SEQ ID NO: 36) |
| VH for A4G10B7A7<br>EVQLVQSGAEVKKPGESLRISCKGSGYSFTSYWISWVRQMPGKGLEWMGRIDPSDSYTNN SPSFQGHVTISVDX1SISTAYLQWSSLKASDTAMYYCARHHPILATISPDAFDIWGQGTMVT VSS (SEQ ID NO: 42, X1 = R)<br>EVQLVQSGAEVKKPGESLRISCKGSGYSFTSYWISWVRQMPGKGLEWMGRIDPSDSYTNN SPSFQGHVTISVDRSISTAYLQWSSLKASDTAMYYCARHHPILATISPDAFDIWGQGTMVT VSS |
| VL for A4G10B7A7<br>EIVLTQSPDTLSLSPGERATLSCRASQSISSRYLAWFQQKPGQAPRLLIHATIRRAT-GIPDRFS GSGSGTDFTLTISGLEPEDFAVYYCQKYSISPYTFGQGTKLEIR (SEQ ID NO: 47) |
| VH CDR1 for A5F3D5A1<br>SYWISWVR (SEQ ID NO: 5) |
| VH CDR2 for A5F3D5A1<br>RIDPSDSYTNNSPSFQG (SEQ ID NO: 12) |
| VH CDR3 for A5F3D5A1<br>HHPILATISPDAFDI (SEQ ID NO: 18) |
| VL CDR1 for A5F3D5A1<br>RASQSISSRYLA (SEQ ID NO: 23) |

-continued

| Description/ Sequence/SEQ ID NO. |
|---|
| VL CDR2 for A5F3D5A1<br>ATIRRAT (SEQ ID NO: 29) |
| VL CDR3 for A5F3D5A1<br>QKYSISPYT (SEQ ID NO: 36) |
| VH for A5F3D5A1<br>EVQLVQSGAEVKKPGESLRISCKGSGYSFTSYWISWVRQMPGKGLEWMGRIDPSDSYTNN SPSFQGHVTISVDX1SISTAYLQWSSLKASDTAMYYCARHHPILATISPDAFDIWGQGTMVT VSS (SEQ ID NO: 42, X1 = K)<br>EVQLVQSGAEVKKPGESLRISCKGSGYSFTSYWISWVRQMPGKGLEWMGRIDPSDSYTNN SPSFQGHVTISVDRSISTAYLQWSSLKASDTAMYYCARHHPILATISPDAFDIWGQGTMVT VSS |
| VL for A5F3D5A1<br>EIVLTQSPDTLSLSPGERATLSCRASQSISSRYLAWFQQKPGQAPRLLIHATIRRAT-GIPDRFS GSGSGTDFTLTISGLEPEDFAVYYCQKYSISPYTFGQGTKLEIR (SEQ ID NO: 47) |
| VH CDR1 for A5G9C2C7<br>GYYMH (SEQ ID NO: 6) |
| VH CDR2 for A5G9C2C7<br>WINPNSGGTNYAQKFQG (SEQ ID NO: 13) |
| VH CDR3 for A5G9C2C7<br>EGLVGVIHGWDV (SEQ ID NO: 19) |
| VL CDR1 for A5G9C2C7<br>RASQNIYNWLA (SEQ ID NO: 24) |
| VL CDR2 for A5G9C2C7<br>KASSLES (SEQ ID NO: 30) |
| VL CDR3 for A5G9C2C7<br>QQYNSNSRT (SEQ ID NO: 37) |
| VH for A5G9C2C7<br>QVQLVQSGAEVKKPGASVKVSCKASGYTFTGYYMHWVRQAPGQGLEWMGWINPNSGG TNYAQKFQGWVTMTRDTSISTAYMELRRLRSDDTAVYYCAREGLVGVIHGWDVWGQGT TVTVSS (SEQ ID NO: 43) |
| VL for A5G9C2C7<br>DIQMTQSPSTLSASVGDRVTITCRASQNIYNWLAWYQQKPGKAPKLLIYKASSLESGVPSR FSGSGSGTEFTLTISSLQPDDFATYYCQQYNSNSRTFGQGTKVEIK (SEQ ID NO: 48) |
| Heavy chain constant region<br>ASTKGPSVFPLAPSSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSREEMTK NQVSLTCLVKGFYPSDIAVEWESNGQPENNYKTTPPVLDSDGSFFLYSKLTVDKSRWQQG NVFSCSVMHEALHNHYTQKSLSLSPGK (SEQ ID NO: 49) |
| Light chain constant region<br>RTVAAPSVFIFPPSDEQLKSGTASVVCLLNNFYPREAKVQWKVDNALQSGNSQESVTEQD SKDSTYSLSSTLTLSKADYEKHKVYACEVTHQGLSSPVTKSFNRGEC (SEQ ID NO: 50) |
| Heavy chain of Eculizumab<br>QVQLVQSGAEVKKPGASVKVSCKASGYIFSNYWIQWVRQAPGQGLEWMGEILPGSGSTE YTENFKDRVTMTRDTSTSTVYMELSSLRSEDTAVYYCARYFFGSSPNWYFDVWGQGTLV TVSSASTKGPSVFPLAPCSRSTSESTAALGCLVKDYFPEPVTVSWNSGALTSGVHTFPAVLQ SSGLYSLSSVVTVPSSNFGTQTYTCNVDHKPSNTKVDKTVERKCCVECPPCPAPPVAGPSV FLFPPKPKDTLMISRTPEVTCVVVDVSQEDPEVQFNWYVDGVEVHNAKTKPREEQFNSTY RVVSVLTVLHQDWLNGKEYKCKVSNKGLPSSIEKTISKAKGQPREPQVYTLPPSQEEMTK NQVSLTCLVKGFYPSDIA VEWESNGQPENNYKTTPPVLDSDGSFFLYSRLTVDKSRWQEG NVFSCSVMHEALHNHYTQKSLSLSLGK (SEQ ID NO: 51) |
| Light chain of Eculizumab<br>DIQMTQSPSSLSASVGDRVTITCGASENIYGALNWYQQKPGKAPKLLIYGATNLADGVPSR FSGSGSGTDFTLTISSLQPEDFATYYCQNVLNTPLTFGQGTKVEIKRTVAAPSVFIFPPSDEQ LKSGTASVVCLLNNFYPREAKVQWKVDNALQSGNSQESVTEQDSKDSTYSLSSTLTLSKA DYEKHKVYACEVTHQG (SEQ ID NO: 52) |
| Heavy chain of Ravulizumab<br>QVQLVQSGAEVKKPGASVKVSCKASGHIFSNYWIQWVRQAPGQGLEWMGEILPGSGHTE |

-continued

| Description/ Sequence/SEQ ID NO. |
|---|
| YTENFKDRVTMTRDTSTSTVYMELSSLRSEDTAVYYCARYFFGSSPNWYFDVWGQGTLV TVSSASTKGPSVFPLAPCSRSTSESTAALGCLVKDYFPEPVTVSWNSGALTSGVHTFPAVLQ SSGLYSLSSVVTVPSSNFGTQTYTCNVDHKPSNTKVDKTVERKCCVECPPCPAPPVAGPSV FLFPPKPKDTLMISRTPEVTCVVVDVSQEDPEVQFNWYVDGVEVHNAKTKPREEQFNSTY RVVSVLTVLHQDWLNGKEYKCKVSNKGLPSSIEKTISKAKGQPREPQVYTLPPSQEEMTK NQVSLTCLVKGFYPSDIA VEWESNGQPENNYKTTPPVLDSDGSFFLYSRLTVDKSRWQEG NVFSCSVLHEALHSHYTQKSLSLSLG (SEQ ID NO: 53) |
| Light chain of Ravulizumab DIQMTQSPSSLSASVGDRVTITCGASENIYGALNWYQQKPGKAPKLLIYGATNLADGVPSR FSGSGSGTDFTLTISSLQPEDFATYYCQNVLNTPLTFGQGTKVEIKRTVAAPSVFIFPPSDEQ LKSGTASVVCLLNNFYPREAKVQWKVDNALQSGNSQESVTEQDSKDSTYSLSSTLTLSKA DYEKHKVYACEVTHQGLSSPVTKSFNRGEC (SEQ ID NO: 54) |
| Heavy chain of Crovalimab QVQLVESGGGLVQPGRSLRLSCAASGFTVHSSYYMAWVRQAPGKGLEWVGAIFTGSGAE YKAEWAKGRVTISKDTSKNQVVLTMTNMDPVDTATYYCASDAGYDYPTHAMHYWGQG TLVTVSSASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKKVEPKSCDKTHTCPPCPAP ELRRGPKVFLFPPKPKDTLMISRTPEVTCVVVDVSHEDPEVKFNWYVDGVEVHNAKTKPR EEQYNSTYRVVSVLTVLHQDWLNGKEYKCKVSNKGLPSSIEKTISKAKGQPREPQVYTLPP SREEMTKNQVSLTCLVKGFYPSDIAVEWESNGQPENNYKTTPPVLDSDGSFFLYSKLTVDK SRWQQGNVFSCSVLHEALHAHYTRKELSLSP (SEQ ID NO: 55) |
| Light chain of Crovalimab DIQMTQSPSSLSASVGDRVTITCRASQGISSSLAWYQQKPGKAPKLLIYGASETESGVPSRF SGSGSGTDFTLTISSLQPEDFATYYCQNTKVGSSYGNTFGGGTKVEIKRTVAAPSVFIFPPSD EQLKSGTASVVCLLNNFYPREAKVQWKVDNALQSGNSQESVTEQDSKDSTYSLSSTLTLS KADYEKHKVYACEVTHQGLSSPVTKSFNRGEC (SEQ ID NO: 56) |
| Heavy chain of Pozelimab QVQLQESGPGLVKPSETLSLTCTVSGDSVSSSYWTWIRQPPGKGLEWIGYIYYSGSSNYNP SLKSRATISVDTSKNQFSLKLSSVTAADTAVYYCAREGNVDTTMIFDYWGQGTLVTVSSA STKGPSVFPLAPCSRSTSESTAALGCLVKDYFPEPVTVSWNSGALTSGVHTFPAVLQSSGLY SLSSVVTVPSSSLGTKTYTCNVDHKPSNTKVDKRVESKYGPPCPPCPAPEFLGGPSVFLFPP KPKDTLMISRTPEVTCVVVDVSQEDPEVQFNWYVDGVEVHNAKTKPREEQFNSTYRVVS VLTVLHQDWLNGKEYKCKVSNKGLPSSIEKTISKAKGQPREPQVYTLPPSQEEMTKNQVS LTCLVKGFYPSDIAVEWESNGQPENNYKTTPPVLDSDGSFFLYSRLTVDKSRWQEGNVFSC SVMHEALHNHYTQKSLSLSLGK (SEQ ID NO: 57) |
| Light chain of Pozelimab AIQMTQSPSSLSASVGDRVTITCRASQGIRNDLGWYQQKPGKAPKLLIYAASSLQSGVPSRF AGRGSGTDFTLTISSLQPEDFATYYCLQDFNYPWTFGQGTKVEIKRTVAAPSVFIFPPSDEQ LKSGTASVVCLLNNFYPREAKVQWKVDNALQSGNSQESVTEQDSKDSTYSLSSTLTLSKA DYEKHKVYACEVTHQGLSSPVTKSFNRGEC (SEQ ID NO: 58) |

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An isolated monoclonal antibody, or an antigen-binding portion thereof, capable of binding to complement component 5, comprising (i) a heavy chain variable region that comprises a $V_H$ CDR1 region, a $V_H$ CDR2 region and a $V_H$ CDR3 region; and (ii) a light chain variable region that comprises a $V_L$ CDR1 region, a $V_L$ CDR2 region and a $V_L$ CDR3 region, wherein the $V_H$ CDR1 region, the $V_H$ CDR2 region, the $V_H$ CDR3 region, the $V_L$ CDR1 region, the $V_L$ CDR2 region and the $V_L$ CDR3 region comprise amino acid sequences set forth in (1) SEQ ID NOs: 1, 7, 14, 20, 25 and 31, respectively; (2) SEQ ID NOs: 2, 8, 15, 20, 26 and 32, respectively; (3) SEQ ID NOs: 2, 8, 16, 20, 25 and 33, respectively; (4) SEQ ID NOs: 3, 9, 17, 21, 27 and 34, respectively; (5) SEQ ID NOs: 4, 10, 18, 22, 28 and 35, respectively; (6) SEQ ID NOs: 4, 11, 18, 22, 28 and 35, respectively; (7) SEQ ID NOs: 4, 12, 18, 23, 29 and 36, respectively; (8) SEQ ID NOs: 5, 12, 18, 23, 29 and 36, respectively; or (9) SEQ ID NOs: 6, 13, 19, 24, 30 and 37, respectively.

2. The isolated monoclonal antibody, or the antigen-binding portion thereof, of claim 1, wherein the heavy chain variable region comprises an amino acid sequence having at least 85%, 86%, 87%, 88%, 89%, 90%, 91%, 92%, 93%, 94%, 95%, 96%, 97%, 98%, 99% or 100% identity to SEQ ID NOs: 38, 39, 40, 41, 42 or 43, wherein $29^{th}$, $71^{st}$, $102^{nd}$ and $107^{th}$ amino acid residues in SEQ ID NO: 39 are I, I, S and F, respectively; or L, M, G and L, respectively;

wherein $58^{th}$ and $60^{th}$ amino acid residues in SEQ ID NO: 41 are T and N respectively; or S and F, respectively, wherein $74^{th}$ amino acid residue in SEQ ID NO: 42 is R or K.

3. The isolated monoclonal antibody, or the antigen-binding portion thereof, of claim 1, wherein the light chain variable region comprises an amino acid sequence having at least 85%, 86%, 87%, 88%, 89%, 90%, 91%, 92%, 93%, 94%, 95%, 96%, 97%, 98%, 99% or 100% identity to SEQ ID NOs: 44, 45, 46, 47, 48, or 59, wherein $18^{th}$, $92^{nd}$ and $106^{th}$ amino acid residues in SEQ ID NO: 44 are S, S and F, respectively; or T, H and I, respectively.

4. The isolated monoclonal antibody, or the antigen-binding portion thereof, of claim 2, wherein the heavy chain variable region and the light chain variable region comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 38 and 44, respectively, wherein $18^{th}$, $92^{nd}$ and $106^{th}$ amino acid residues in SEQ ID NO: 44 are S, S and F, respectively;

(2) SEQ ID NOs: 39 and 59, respectively, wherein $29^{th}$, $71^{st}$, $102^{nd}$ and $107^{th}$ amino acid residues in SEQ ID NO: 39 are I, I, S and F, respectively;

(3) SEQ ID NOs: 39 and 44, respectively, wherein $29^{th}$ $71^{st}$, $102^{nd}$ and $107^{th}$ amino acid residues in SEQ ID NO: 39 are L, M, G and L, respectively, wherein $18^{th}$, $92^{nd}$ and $106^{th}$ amino acid residues in SEQ ID NO: 44 are T, H and I, respectively;

(4) SEQ ID NOs: 40 and 45, respectively;

(5) SEQ ID NOs: 41 and 46, respectively, wherein $58^{th}$ and $60^{th}$ amino acid residues in SEQ ID NO: 41 are T and N respectively;

(6) SEQ ID NOs: 41 and 46, respectively, wherein $58^{th}$ and $60^{th}$ amino acid residues in SEQ ID NO: 41 are S and F, respectively;

(7) SEQ ID NOs: 42 and 47, respectively, wherein $74^{th}$ amino acid residue in SEQ ID NO: 42 is R;

(8) SEQ ID NOs: 42 and 47, respectively, wherein $74^{th}$ amino acid residue in SEQ ID NO: 42 is K; or (9) SEQ ID NOs: 43 and 48, respectively.

5. The isolated monoclonal antibody, or the antigen-binding portion thereof, of claim 1, comprising a heavy chain constant region comprising an amino acid sequence of SEQ ID NO: 49, linked to the heavy chain variable region, and a light chain constant region comprising an amino acid sequence of SEQ ID NO: 50, linked to the light chain variable region.

6. The isolated monoclonal antibody, or the antigen-binding portion thereof, of claim 1, which is an IgG1, IgG2 or IgG4 isotype.

7. The isolated monoclonal antibody, or the antigen-binding portion thereof, of claim 1, which is able to (a) bind wild-type human C5; (b) bind human C5 carrying R885C mutation; (c) bind monkey C5; and (d) block complement-mediated hemolysis.

8. The isolated monoclonal antibody, or the antigen-binding portion thereof, of claim 1, which is a human antibody or antigen-binding portion thereof.

9. A nucleotide encoding the isolated monoclonal antibody or the antigen-binding portion thereof of claim 1.

10. An expression vector comprising the nucleotide of claim 9.

11. A host cell comprising the expression vector of claim 10.

12. A pharmaceutical composition comprising the isolated monoclonal antibody, or antigen-binding portion thereof, of claim 1, and a pharmaceutically acceptable carrier.

13. The pharmaceutical composition of claim 12, further comprising anti-inflammatory agent.

14. A method for blocking complement-mediated hemolysis, comprising contacting red blood cells with the isolated monoclonal antibody or the antigen-binding portion thereof of claim 1.

15. An antibody, or an antigen-binding portion thereof, capable of binding to complement component 5, comprising a heavy chain variable region and a light chain variable region, wherein the heavy chain variable region and the light chain variable region comprise amino acid sequences having at least 85%, 86%, 87%, 88%, 89%, 90%, 91%, 92%, 93%, 94%, 95%, 96%, 97%, 98%, 99% or 100% identity to (1) SEQ ID NOs: 38 and 44, respectively, wherein $18^{th}$, $92^{nd}$ and $106^{th}$ amino acid residues in SEQ ID NO: 44 are S, S and F, respectively;

(2) SEQ ID NOs: 39 and 59, respectively, wherein $29^{th}$, $71^{st}$, $102^{nd}$ and $107^{th}$ amino acid residues in SEQ ID NO: 39 are I, I, S and F, respectively;

(3) SEQ ID NOs: 39 and 44, respectively, wherein $29^{th}$, $71^{st}$, $102^{nd}$ and $107^{th}$ amino acid residues in SEQ ID NO: 39 are L, M, G and L, respectively, wherein $18^{th}$, $92^{nd}$ and $106^{th}$ amino acid residues in SEQ ID NO: 44 are T, H and I, respectively;

(4) SEQ ID NOs: 40 and 45, respectively;

(5) SEQ ID NOs: 41 and 46, respectively, wherein $58^{th}$ and $60^{th}$ amino acid residues in SEQ ID NO: 41 are T and N respectively;

(6) SEQ ID NOs: 41 and 46, respectively, wherein $58^{th}$ and $60^{th}$ amino acid residues in SEQ ID NO: 41 are S and F, respectively;

(7) SEQ ID NOs: 42 and 47, respectively, wherein $74^{th}$ amino acid residue in SEQ ID NO: 42 is R;

(8) SEQ ID NOs: 42 and 47, respectively, wherein $74^{th}$ amino acid residue in SEQ ID NO: 42 is K; or (9) SEQ ID NOs: 43 and 48, respectively.

* * * * *